(12) United States Patent
Kessler et al.

(10) Patent No.: US 12,048,485 B2
(45) Date of Patent: Jul. 30, 2024

(54) SURGERY 3D VISUALIZATION APPARATUS

(71) Applicant: Raytrx, LLC, Tulsa, OK (US)

(72) Inventors: David Kessler, New York, NY (US); Michael H. Freeman, Tulsa, OK (US); Mitchael C. Freeman, Tulsa, OK (US); Simon Prosser, Tulsa, OK (US); Jordan Boss, Tulsa, OK (US); Steven Yeager, Tulsa, OK (US); Cuong Vu, Tulsa, OK (US); Linda A. Lam, Tulsa, OK (US); Montgomery Freeman, Tulsa, OK (US); Steven Von der Porten, Tulsa, OK (US); Dillon Cornell, Tulsa, OK (US)

(73) Assignee: RAYTRX, LLC, Tulsa, OK (US)

( * ) Notice: Subject to any disclaimer, the term of this patent is extended or adjusted under 35 U.S.C. 154(b) by 0 days.

(21) Appl. No.: 17/712,535

(22) Filed: Apr. 4, 2022

(65) Prior Publication Data
US 2022/0313085 A1    Oct. 6, 2022

Related U.S. Application Data

(60) Provisional application No. 63/170,718, filed on Apr. 5, 2021.

(51) Int. Cl.
*A61B 3/14* (2006.01)
*A61B 3/135* (2006.01)

(52) U.S. Cl.
CPC ................ *A61B 3/14* (2013.01); *A61B 3/135* (2013.01)

(58) Field of Classification Search
CPC ........ G02B 21/004; G02B 21/22; A61B 3/13; A61B 3/14; A61B 3/135
USPC .......................................................... 351/206
See application file for complete search history.

(56) References Cited

U.S. PATENT DOCUMENTS

| | | | | |
|---|---|---|---|---|
| 2,590,101 | A * | 3/1952 | Henschke | A61B 5/163 434/179 |
| 4,669,837 | A * | 6/1987 | Schirmer | B23K 26/032 351/205 |
| 4,786,161 | A * | 11/1988 | Muller | A61B 3/156 351/205 |
| 5,249,004 | A * | 9/1993 | Kitajima | A61B 3/13 351/205 |
| 5,321,446 | A * | 6/1994 | Massig | A61B 3/135 351/215 |
| 5,907,431 | A * | 5/1999 | Stuttler | G02B 21/22 250/201.3 |
| 5,912,722 | A * | 6/1999 | Schirmer | A61B 3/135 351/205 |
| 6,634,750 | B2 * | 10/2003 | Neal | G01M 11/0264 351/211 |
| 6,943,942 | B2 * | 9/2005 | Horiguchi | G02B 21/06 359/383 |

(Continued)

*Primary Examiner* — Zachary W Wilkes
(74) *Attorney, Agent, or Firm* — Howard & Howard Attorneys PLLC

(57) ABSTRACT

An apparatus for obtaining an image of a cornea having a stereomicroscope configured to obtain and display 2D or 3D image content of an eye of a patient, with pupil imaging optics that form a pupil along an optical axis and a shutter configured to form a pattern of one or more apertures for light at the formed pupil. An input prism is configured to direct light to or from the optical axis, with optics configured to convey light along the optical axis to a sensor.

17 Claims, 29 Drawing Sheets

(56) References Cited

U.S. PATENT DOCUMENTS

| | | | |
|---|---|---|---|
| 7,019,780 B1* | 3/2006 | Takeuchi | H04N 13/211 348/340 |
| 8,363,156 B2* | 1/2013 | Lo | G03B 35/04 348/220.1 |
| 8,625,981 B2* | 1/2014 | Takada | G03B 9/08 396/458 |
| 8,922,624 B2* | 12/2014 | Pretorius | G02B 21/22 348/46 |
| 9,826,901 B2* | 11/2017 | Kim | A61B 3/135 |
| 10,146,040 B2* | 12/2018 | Schnitzler | G02B 21/025 |
| 2002/0080478 A1* | 6/2002 | Mannss | G02B 21/0012 359/368 |
| 2003/0038921 A1* | 2/2003 | Neal | G01M 11/0264 351/212 |
| 2003/0120266 A1 | 6/2003 | Fujieda | |
| 2004/0155975 A1* | 8/2004 | Hart | G02B 21/361 348/335 |
| 2007/0247691 A1* | 10/2007 | Obrebski | G02B 21/0012 359/227 |
| 2008/0174869 A1 | 7/2008 | Cathey et al. | |
| 2009/0122398 A1* | 5/2009 | Machida | G02B 21/0012 359/388 |
| 2010/0157244 A1 | 6/2010 | LeBlanc | |
| 2011/0242287 A1* | 10/2011 | Cieslinski | G02B 30/24 396/323 |
| 2012/0008195 A1* | 1/2012 | Hoegele | G02B 21/025 359/380 |
| 2012/0013849 A1* | 1/2012 | Podoleanu | A61B 3/1005 351/221 |
| 2012/0062839 A1 | 3/2012 | Su et al. | |
| 2016/0227998 A1* | 8/2016 | Schmoll | A61B 3/156 |
| 2016/0235288 A1* | 8/2016 | Henriksen | A61B 3/125 |
| 2017/0276954 A1 | 9/2017 | Bajorins et al. | |
| 2019/0209372 A1* | 7/2019 | Farley | H04J 14/08 |
| 2022/0075167 A1* | 3/2022 | Bor | A61B 3/14 |

\* cited by examiner

SURGERY 3D VISUALIZATION APPARATUS

CROSS REFERENCE TO RELATED APPLICATIONS

The present application claims the benefit of U.S. Provisional application Ser. No. 63/170,718, provisionally filed on Apr. 5, 2021 entitled "SURGERY 3D VISUALIZATION APPARATUS" in the names of David Kessler, Ph.D., Michael H. Freeman, J. D., et al., incorporated herein by reference in its entirety.

FIELD OF THE DISCLOSURE

The present disclosure generally relates to optical apparatus for clinical and surgical use and more particularly to a system for acquisition and display in ophthalmology for visualization of the cornea, iris and vitreous humour under examination and treatment.

BACKGROUND

Continuing advances in medical treatment have been provided using improved systems for visualization, helping to support the medical practitioner with advanced functions and features that employ aspects of digital image acquisition, processing, and display. Handling image content in digital form, in turn, allows advanced surgical support systems to provide automated functions that include robotic procedural assistance, telemedicine applications, and application of Machine Learning (ML) and Artificial Intelligence (AI).

In many cases, digital image acquisition (still or video image) and visualization tools have been added to legacy systems that were designed for use with analog and some earlier electronic visualization tools, limiting the abilities of full digital applications. Such earlier systems provide some level of advancement, but often suffer from poor ergonomics and are not readily modified or adaptable for taking better advantage of digital processing and display capabilities.

Systems especially useful for ophthalmology present a particular challenge, due to factors including complexity of the optical path, space constraints, difficulties related to brightness, and disappointing resolution. Ophthalmoscopic exam techniques, such as a slit-lamp exam, are widely used for eye examination. Various tools designed for these procedures have taken some advantage of digital imaging tools, but the overall procedure for ophthalmoscopic exam remains a highly manual process. For example, typical ophthalmoscopic exam procedures require accurate positioning of the practitioner for observation as well as careful positioning, by the practitioner, of an objective lens very near the patient's cornea and at the proper angle relative to a bright light source that is worn by the practitioner. These criteria require an expert surgeon or practitioner to operate.

Inherent problems that have negative impact upon overall cornea examination practices and the patient experience, and tend to degrade image quality, include difficulties in obtaining sufficient illumination and low patient tolerance to bright lighting. In particular, slit-lamp examination requires an extremely bright light source, introducing risk concerns for phototoxicity, and offering a very limited viewing area. These constraints can negatively affect diagnosis of eye pathology, which can even result in incorrect diagnosis or failure to detect some types of conditions.

The stereomicroscope is a widely used tool in ophthalmology, particularly for intraocular surgery. Particular challenges for this device include the following:
(i) need to image all portions of the eye in 3D, for both the cornea and the retina;
(ii) need to switch easily from anterior to posterior imaging;
(iii) need for systems where the components in close proximity to the patient can be readily sterilized to reduce operation time and cost;
(iv) requirements for patient safety during operation;
(v) need for improved surgeon ergonomics;
(vi) poor visibility of various features within the eye due to the limited aperture sizes of the 3D apertures;
(vii) need for higher resolution to aid in detection;
(viii) need for wide angle visibility of the retina;
(ix) need for image rectification;
(x) need to reduce microscope size to reduce patient obscuration and to allow maneuverability of the microscope for orientation at different viewing angles;
(xi) need to be able to readily switch from lower resolution 3D mode to a high-resolution mesoscopic and monoscopic viewing-mode; and
(xii) need to be usable with both intra-vitreous illumination and external illumination.

Faced with these challenges, stereomicroscopy design has provided some solutions, but there is considerable room for improvement. It can be appreciated that there is a need for improved visualization apparatus and approaches for support of ophthalmoscopy and other functions used for detailed patient examination and treatment.

SUMMARY OF THE INVENTION

The Applicants address the problem of advancing the art of digital acquisition and visualization for examination and surgical applications. Acquired microscope and resulting still or video 2D and 3D images can be magnified by virtue of optical zoom, as described herein, and digital zoom together which provide the magnification in embodiments of the present disclosure.

With this object in mind, there is provided an ophthalmic stereomicroscopy apparatus for obtaining an image of a cornea comprising:
  pupil imaging optics that form a pupil along an optical axis;
  a shutter configured to form a pattern of one or more apertures for light at the formed pupil and allowing 3d imaging sequentially an input prism configured to direct light to or from the optical axis; and
  optics configured to convey light along the optical axis to a sensor.

The system can be compact and maneuverable, usable in surgery with the patient horizontally disposed or usable in the optometrist or ophthalmologist office environment for eye examination, with the patient vertically disposed (such as seated or standing).

The practitioner can switch from 3D mode to monoscope mode for higher resolution and improved Signal-to-Noise Ratio (SNR). The practitioner can also change the degree of stereopsis and azimuth angular offset.

The practitioner can obtain 2D or 3D imagery while avoiding imperfections on the patient cornea or iris. The system allows both conventional illumination with an auxiliary illumination unit or with coaxial illumination.

The system can be used in combination with a retinal imaging system such as is shown in FIG. 12. The system may use a combination of elements or two systems mounted adjacently on a microscope turret, as shown in FIG. 13A, with the systems selectable by the practitioner using electronic or mechanical selection means. The cornea imaging attachment described herein can be used as a standalone imaging device, typically useful for office examination by the practitioner. When mounted as part of a larger imaging system, the cornea imaging attachment can be mounted in the turret of FIG. 13A or other type of switching device and used to automate office examination imaging as well as for imaging during surgical procedures. Robotic actuators, not shown, can be used to position and increment the imaging attachment at different angles for more complete imaging content.

Unlike a slit-lamp or direct or indirect ophthalmoscopy examinations, which take place with the naked eyes of the physician, this method provides the added improvement of taking and presenting still or video images (collectively, "video") to record and, if needed, to use for subsequent examination.

DRAWINGS

DETAILED DESCRIPTION

Figure 1A:
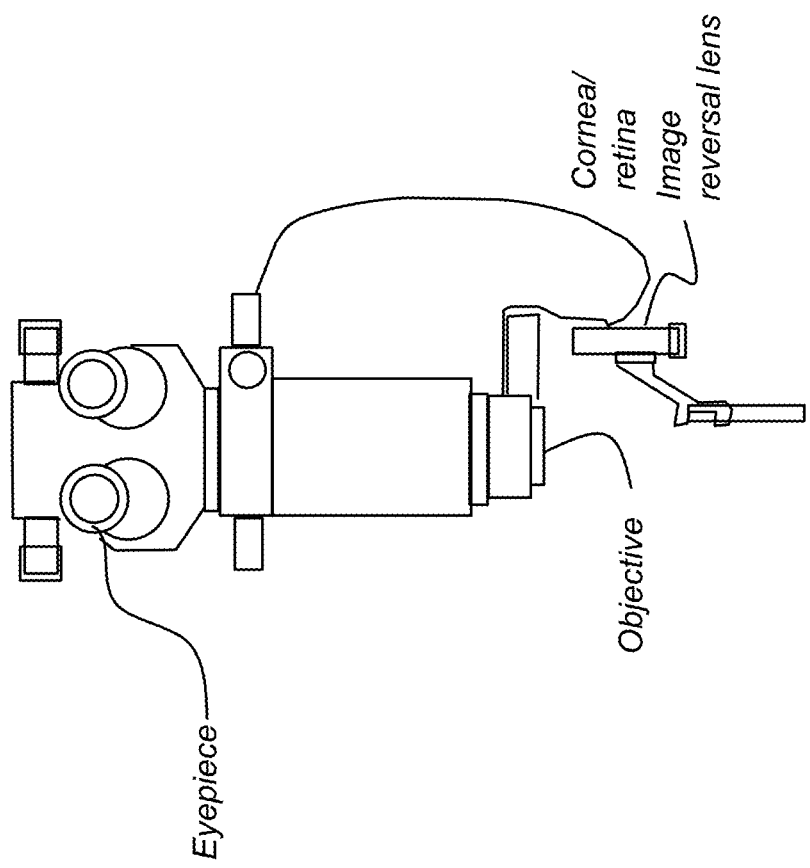
FIG. 1A is a schematic diagram showing portions of a conventional microscope imaging apparatus that is designed for examination, in a first mode, of the cornea and near structures of the eye and, in a second mode, for examination of the retina.

The following is a detailed description of the preferred embodiments of the disclosure, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification. It will be apparent to one having ordinary skill in the art that the specific detail need not be employed to practice according to the present disclosure. In other instances, well-known materials or methods have not been described in detail in order to avoid obscuring the present disclosure.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples.

In the context of the present disclosure, the term "coupled" is intended to indicate a mechanical association, connection, relation, or linking, between two or more components, such that the disposition of one component affects the spatial disposition of a component to which it is coupled.

For mechanical coupling, two components need not be in direct contact, but can be linked through one or more intermediary components.

With particular respect to electronic signal content, several (or different) elements discussed herein and/or claimed are described as being "coupled," "in communication with," "integrated," or "configured to be in signal communication with" or a "system" or "subsystem" thereof. This terminology is intended to be non-limiting and, where appropriate, can be interpreted to include, without limitation, wired and wireless communication using any one or a plurality of a suitable protocols, as well as communication methods that are constantly maintained, are made on a periodic basis, and/or made or initiated on an as-needed basis.

Some portions of embodiments in accordance with the present disclosure may be embodied as a system, an apparatus, a method, a computer program, hardware/software, and/or product, including encoded instructions on a transitory or non-transitory computer-readable storage medium. All of the systems and subsystems may exist, or portions of the systems and subsystems may exist to form the solution of the present disclosure. Accordingly, the apparatus of the present disclosure may take the form of an entirely hardware embodiment, an entirely software embodiment (including firmware, resident software, micro-code, etc.), or an embodiment combining software and hardware aspects that may all generally be referred to herein as a "unit," "module," or "system." Furthermore, the apparatus of the present disclosure may take the form of a computer program product embodied in any tangible media of expression having computer-usable program code embodied in the media. Any combination of one or more computer-usable or computer-readable media (or medium) may be utilized. For example, a random-access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Further, the intelligence in the main logic circuitry may be software, firmware, or hardware, and can be microcontroller based or included in a state machine. The apparatus of the present disclosure may be a combination of the above intelligence and memory, and this can exist in a central processing unit or a multiple of chips including a central graphics chip. The computer portion of the apparatus of the present disclosure may also include a model view controller (MVC) or "model controller."

The cornea imaging attachment described herein can be used as a standalone imaging device or can be used as part of a larger imaging system. This attachment can be used for office examination imaging as well as for imaging during surgical procedures.

The schematic diagram of FIG. 1A shows portions of a conventional microscope imaging apparatus that is designed for examination, in a first mode, of the cornea and near structures of the eye and, in a second mode, for examination of the retina. Image reversal occurs with change of mode. A lens attachment enables switching for between modes.

Figure 1B:
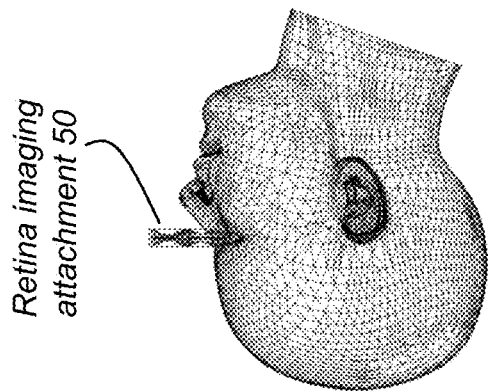
FIG. 1B is a schematic diagram showing use of a cornea imaging attachment according to an embodiment of the present disclosure.
Figure 1B:
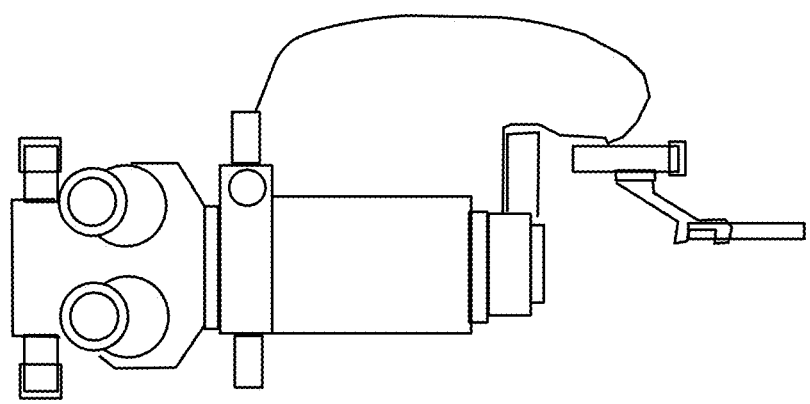
Figure 1B:
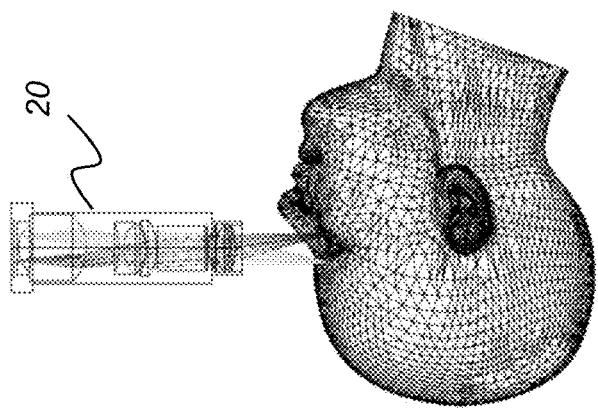

The schematic diagram of FIG. 1B shows a comparison of relative size and use for a cornea imaging attachment according to an embodiment of the present disclosure. Also shown is a retina imaging attachment 50.

Structure of the Cornea Imaging Attachment

Figure 1C:
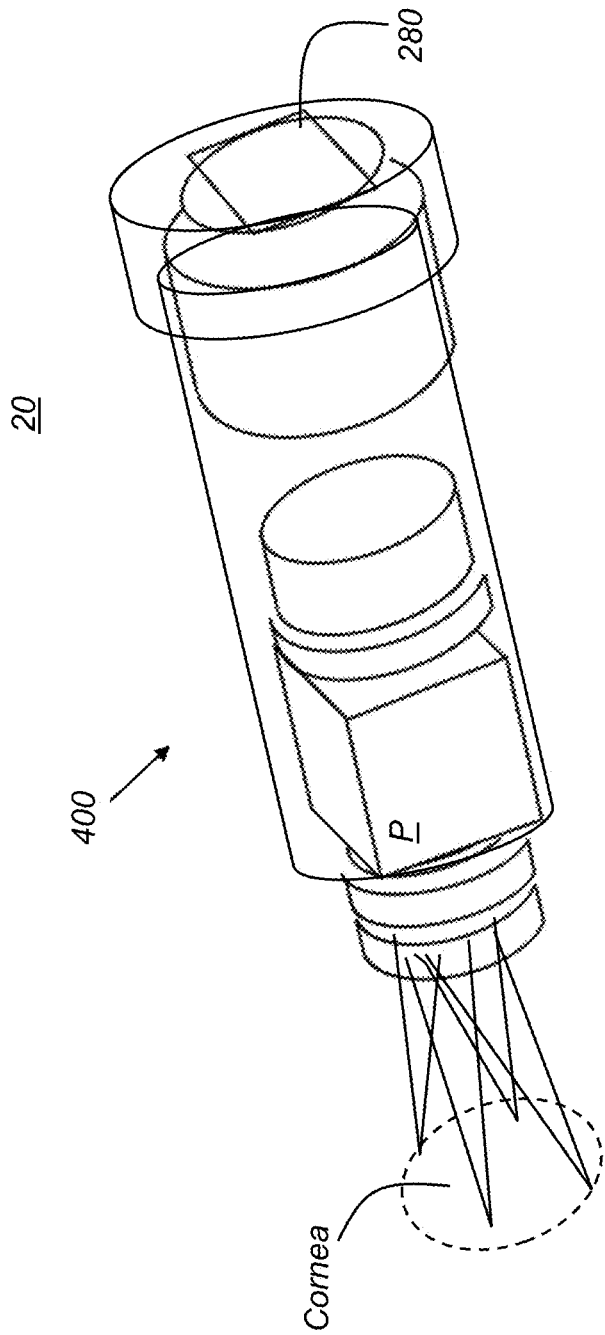
FIG. 1C is a perspective view that shows a compact cornea imager according to an embodiment of the present disclosure.

FIG. 1C is a perspective view that shows a compact cornea imaging attachment 20 according to an embodiment of the present disclosure.

The cornea imaging attachment 20 has pupil imaging optics 210 that form an optical pupil along an optical axis OA. A shutter S is configured to form a pattern of one or more apertures for light at the formed pupil. An input prism P is configured to direct light to or from the optical axis. Additional optics are configured to convey light along the optical axis to a sensor 280 that obtains the image data. Image sensor 280 is in signal communication with a system processor that records the data and can provide the data for display, storage, or transmission as needed.

Sterilization

In the event of contact with the patient, the examination procedure using the cornea attachment 20 is interrupted and a sterilization cycle must be executed. This procedure can involve numerous steps for proper removal and re-seating of equipment and for the sterilization regimen.

As shown in FIG. 1C, embodiments of the present disclosure can provide enclosure of the optics system within a cylindrical housing 400. This enclosure can be formed of polycarbonate or other suitable material. When sterilization is required, the housing 400 enclosure can be replaced. The housing 400 enclosure can be a disposable element or it could be reusable, replaced as necessary with a previously autoclaved unit, for example.

Autostereoscopic Imaging:

Stereoscopic imaging of a subject requires image content provided from two perspectives. Using cornea imaging attachment 20, 3D imaging can be achieved by forming two sub-apertures, optically disposed at the patient's iris, and obtaining the cornea images from these two sub apertures, with a convergence angle provided between the sub-apertures.

In conventional apparatus, two sub-apertures are formed at the large objective of the microscope. Commonly, the objective has a diameter of 3 inches, in which two sub apertures, each of about 1.25-inch diameter, are placed side by side. The objective is at a working distance (WD) of about 200 mm (approx. 8 inches) from the cornea. Thus, the objective has NA (numerical aperture) of 0.1875 when used with the two sub-apertures. As a consequence, adequate stereopsis is provided to the viewing practitioner.

Figure 2:
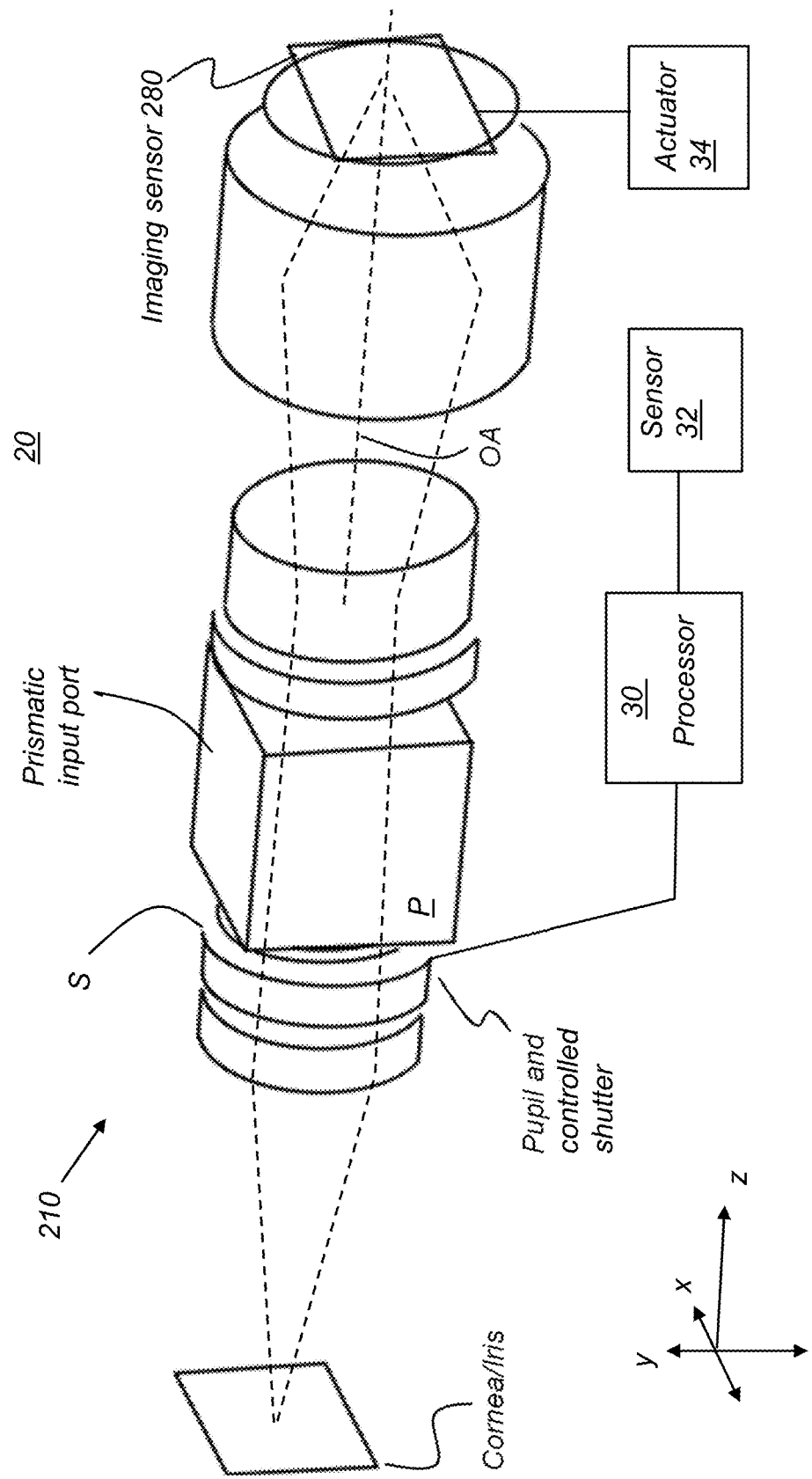
FIG. 2 is a perspective schematic diagram showing the cornea imager of FIG. 1C in more detail including a shutter.

The compact cornea imager of the present disclosure, as shown in FIGS. 1C and 2, has a working distance (WD) of 61 mm from the cornea, with an objective diameter of less than 1.5 inches. The NA=0.1875 matches that of the conventional system, thus allowing a comparable match to the level of stereopsis provided by the much larger conventional stereomicroscope.

In conventional apparatus, the images obtained from two sub-apertures are conveyed to the practitioner's eyes respectively and/or to two cameras or imaging sensors 280. In embodiments of the present disclosure, no eyepieces are used. Thus, positioning constraints for the viewing practitioner are relaxed. The imager can be more readily aligned and aimed to examine the patient at different angles as shown subsequently in FIGS. 6A, 6B.

Figure 14:
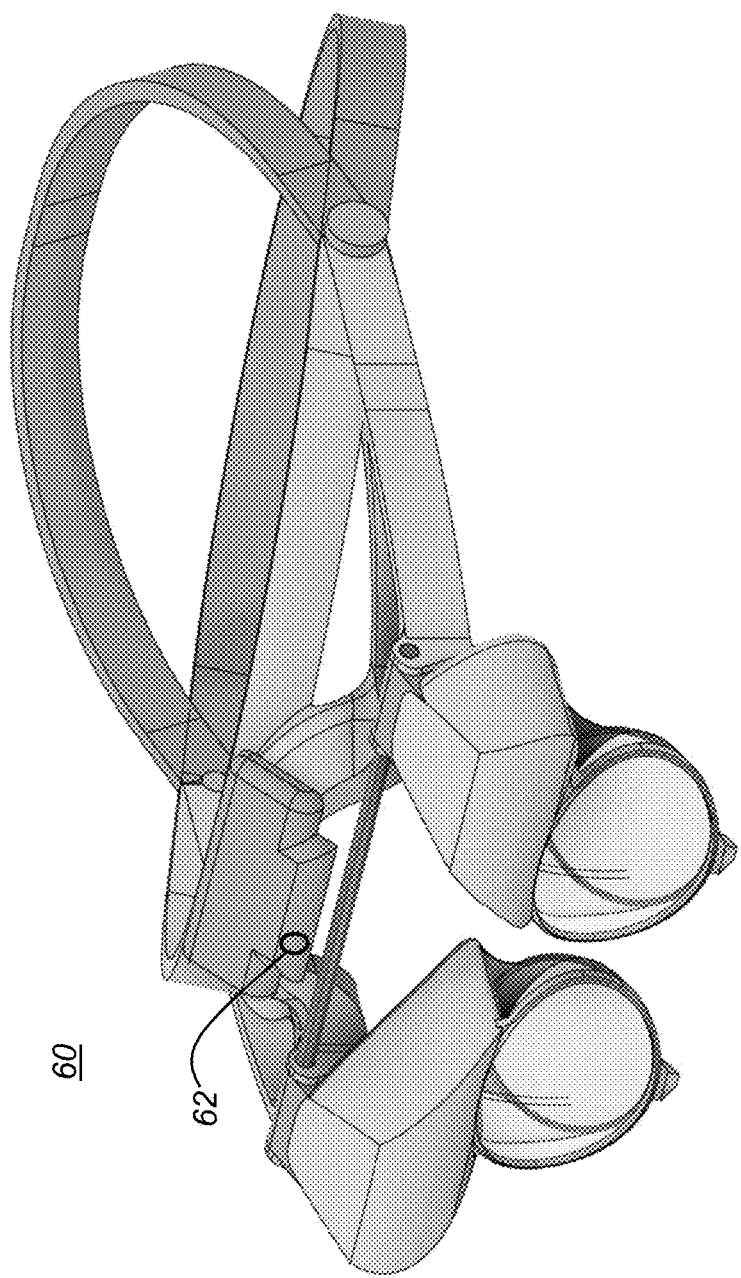
FIG. 14 shows an AR headset for viewing images of the cornea and related features.
Figure 15:
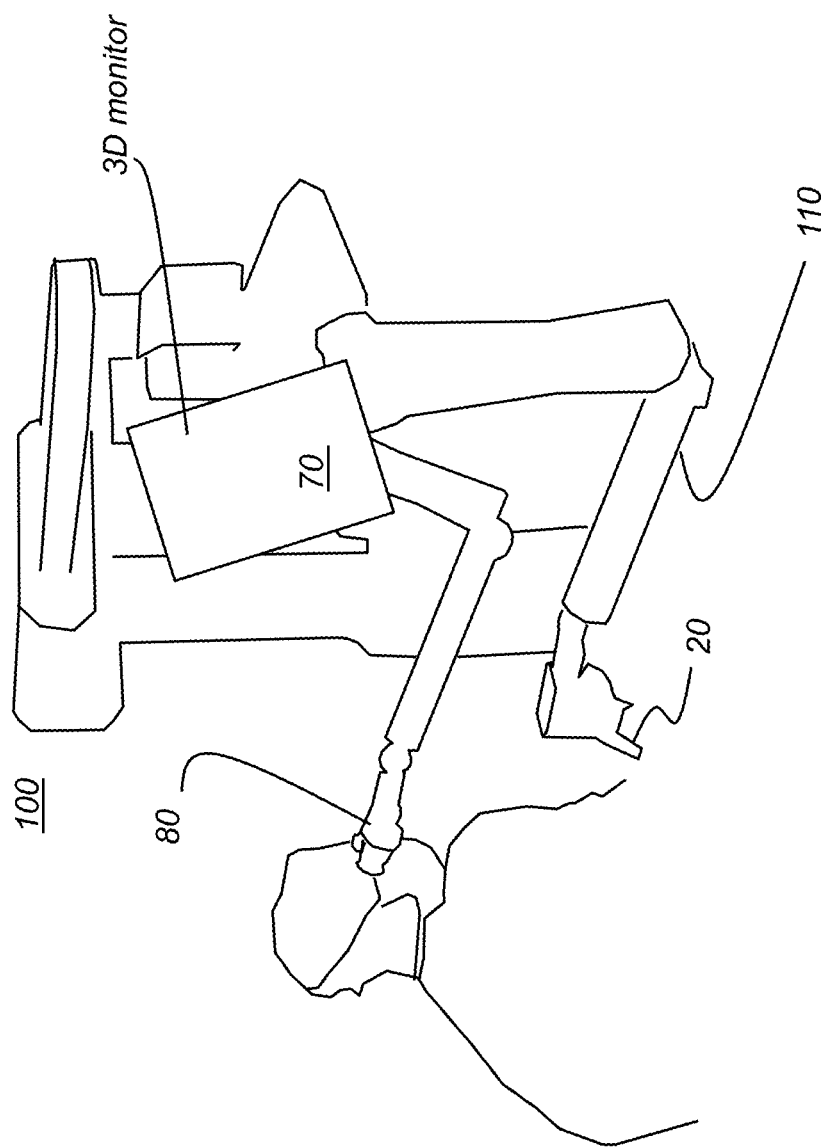
FIG. 15 shows a 3D monitor.

Alternatively, the 2D or 3D image formed by the camera or image sensors can be transmitted in wired or wireless form to an imager such as an AR/XR wireless headset 60, as shown in FIG. 14, or to a 3D monitor, which could be an 3D "glasses free" autostereoscopic monitor 70 as shown in FIG. 15.

Figure 3:
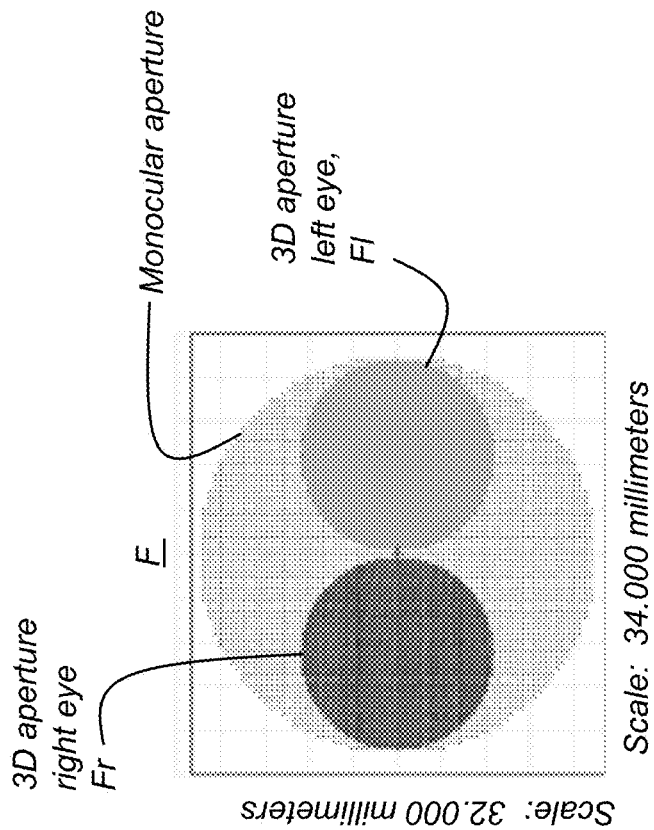
FIG. 3 is a plan view showing a pattern of apertures at the shutter.

Referring to FIGS. 2 and 3, an embodiment of the present disclosure uses a pupil shutter S having a variable aperture arrangement. A control logic processor 30 is programmed with instructions to execute shutter S control to allow selection of either 3D or monoscopic image content. Using shutter S control of aperture patterns, as shown in the examples of FIGS. 5A-5D and FIGS. 7A-9B, cornea imaging attachment 20 can be switched from a monoscopic mode having a single larger aperture, advantaged for its higher resolution, to a sequential 3D mode that employs two smaller apertures, one for each eye, alternately switched into view in sequence. Resolution is the trade-off: the resolution of each of the images obtained by the small sub-apertures is significantly lower compared with the resolution obtained through the full iris aperture, since the diffraction spot size is dependent on the aperture size.

As conventional 3D microscopes have been constructed, the image content is either provided at higher monoscopic resolution or at lower resolution for stereoscopic imaging. With conventional systems, the surgeon cannot switch at will from a 3D view to higher resolution monoscopic imaging, such as in the middle of an eye exam. In an embodiment of the present disclosure, however, by controlling the aperture pattern formed using an electronically controlled shutter S that is formed using a spatial light modulator, the surgeon can readily switch between monoscopic and 3D vision. The schematic diagram of FIG. 3 briefly shows an allocation of the field of view (FOV) F that can be provided by controlling the shutter S aperture(s).

Figure 4A:
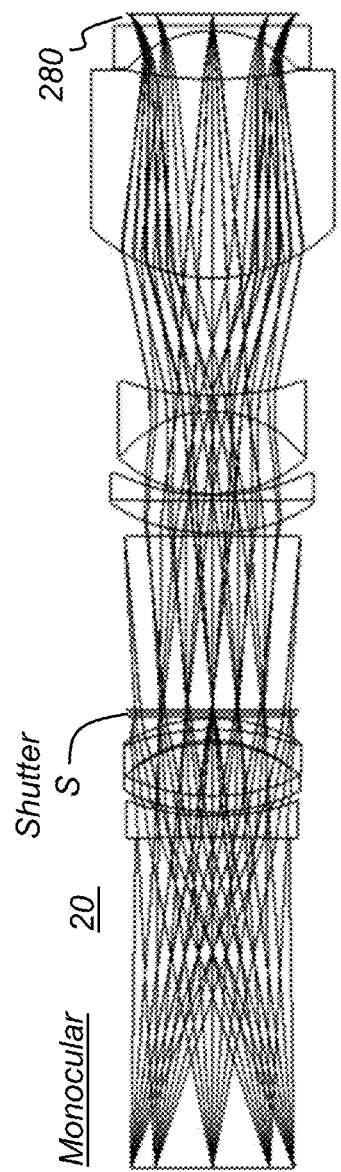
FIG. 4A is a side view schematic showing components of the cornea imaging attachment for monoscopic full aperture imaging.

A monoscopic or monocular view can use the full aperture field F as shown in FIG. 3. The optical path for monoscopic viewing is shown in side view schematic form in FIG. 4A.

Figure 4B:
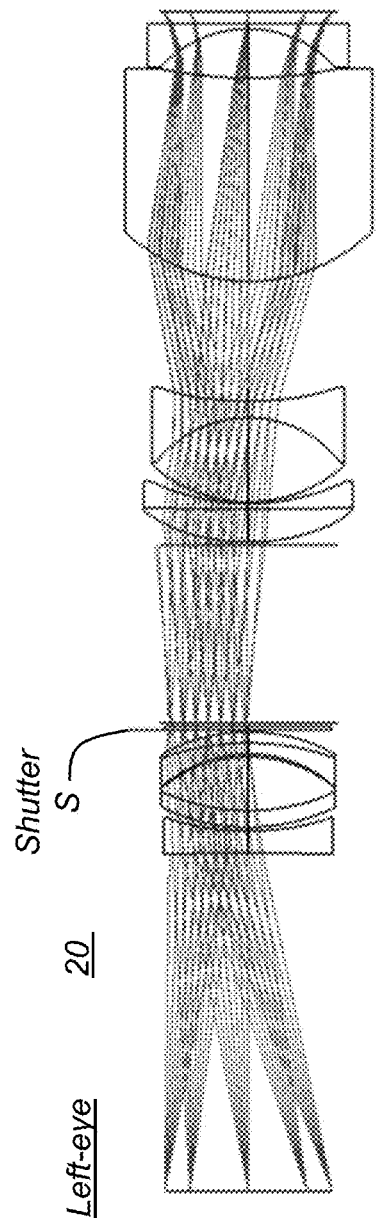
FIGS. 4B and 4C are side view schematics showing components of the cornea imaging attachment for stereoscopic imaging.
Figure 4C:
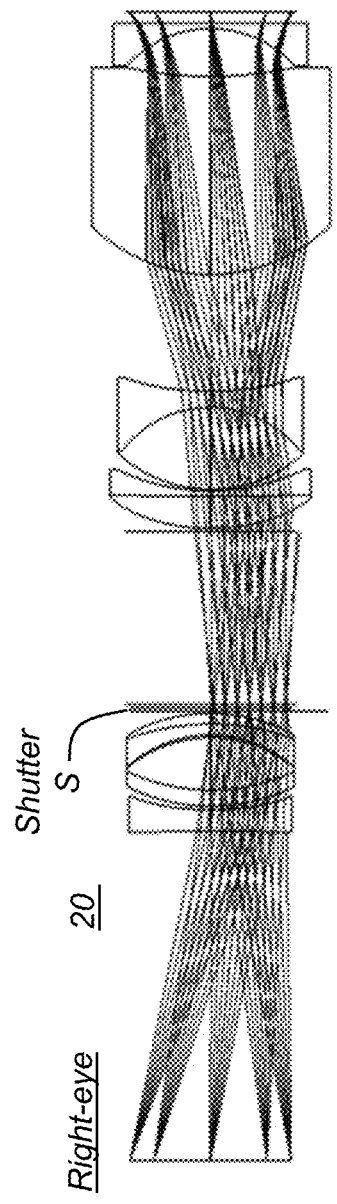
Figure 5A:
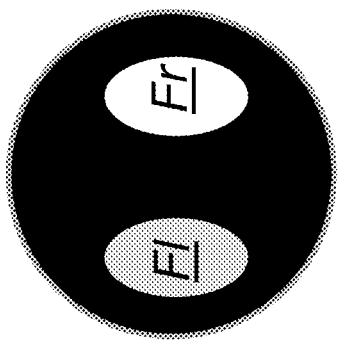
FIGS. 5A-5D show aperture arrangements that can be used at the shutter for stereoscopic and monoscopic imaging.
Figure 5B:
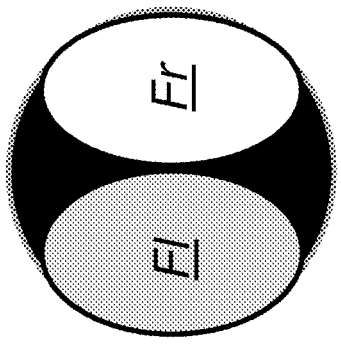

FIGS. 4B and 4C show light paths, shown for left- and right-eye views, respectively, when smaller sub-apertures are used for stereoscopic viewing. To obtain the stereoscopic view using the optical paths of FIGS. 4B and 4C, shutter S can be switched to alternate rapidly between left- and right-eye content, as shown in FIGS. 5A and 5B.

Shutter S can be controlled by a control logic processor 30, which can be a dedicated microprocessor or other control logic device that is part of the stereomicroscope imaging apparatus. Shutter S can be a liquid crystal device (LCD) array, a micro-electromechanical systems (MEMS) device or other configurable type of spatial light modulator that is capable of switching to provide different apertures at sufficient speed, for example.

A command or instruction to configure the aperture or apertures formed by shutter S can be entered using a keyboard instruction on a control console or by entering a command on a touchscreen or keypad, for example. According to an alternate embodiment of the present disclosure, the viewing practitioner can enter an audible instruction or use a gestural command, such as a head or hand movement, sensed by a sensor 32 (FIG. 2), such as a microphone or a camera or other sensor. Control logic processor 30 can be programmed or can use machine-learning logic to select either a stereoscopic or monoscopic arrangement for apertures of shutter S, depending on the type of exam, practitioner preference, or other factors.

By controlling the size and position of shutter S apertures, the images can be obtained sequentially for the right and left eye, where each image is viewed through the corresponding sub aperture at the iris. In addition, using configurable apertures, spacing between apertures can be changed according to viewer instructions, such as customizing view conditions for a particular user, in order to adjust visibility for suitable viewer interocular or inter-pupil distance (IPD). Apertures can be any suitable shape, such as round, elliptical, or other shape and can be horizontally distributed with respect to each other or at some angle oblique (that is, not an integer multiple of 90 degrees) to horizontal, such as at 10, 20, or 30 degrees with respect to each other, or at some other oblique angle from 1 to 89 degrees with respect to each other as needed. Aperture shape can also be adjusted using operator instructions, such as for changing from round to elliptical, or to change the eccentricity of an elliptical aperture to adjust image contrast, for example.

Figure 5C:
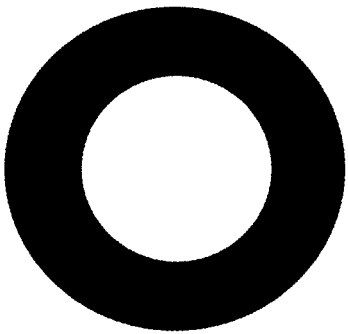
Figure 5D:
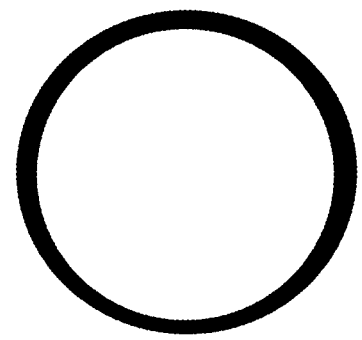
Figure 6B:
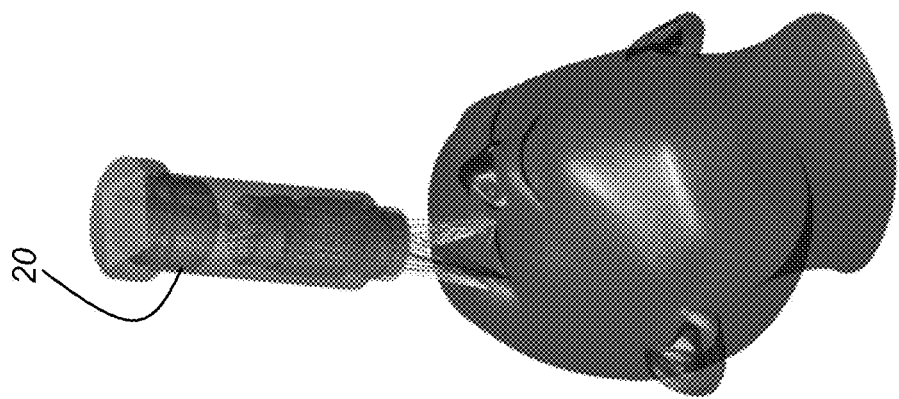
FIGS. 6A and 6B show the cornea microscope attachment as used in surgery, aimed into the patient eye at different angles to cover different cornea regions.
Figure 6A:
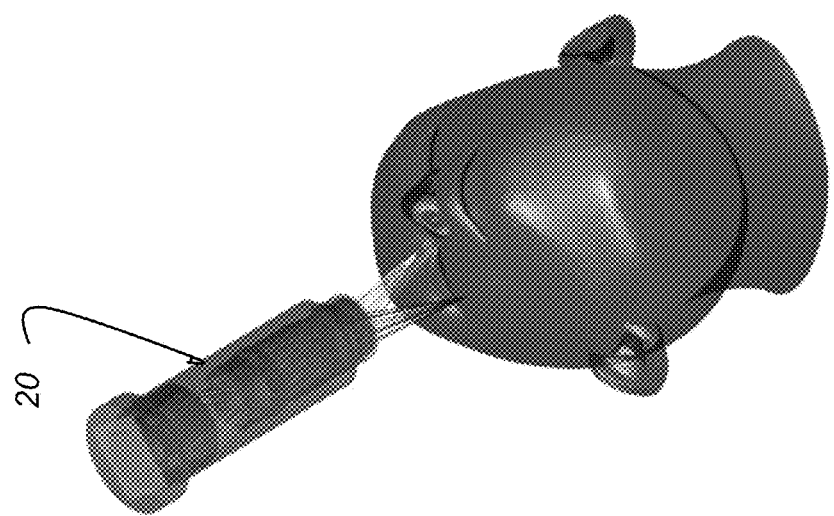
Figure 6C:
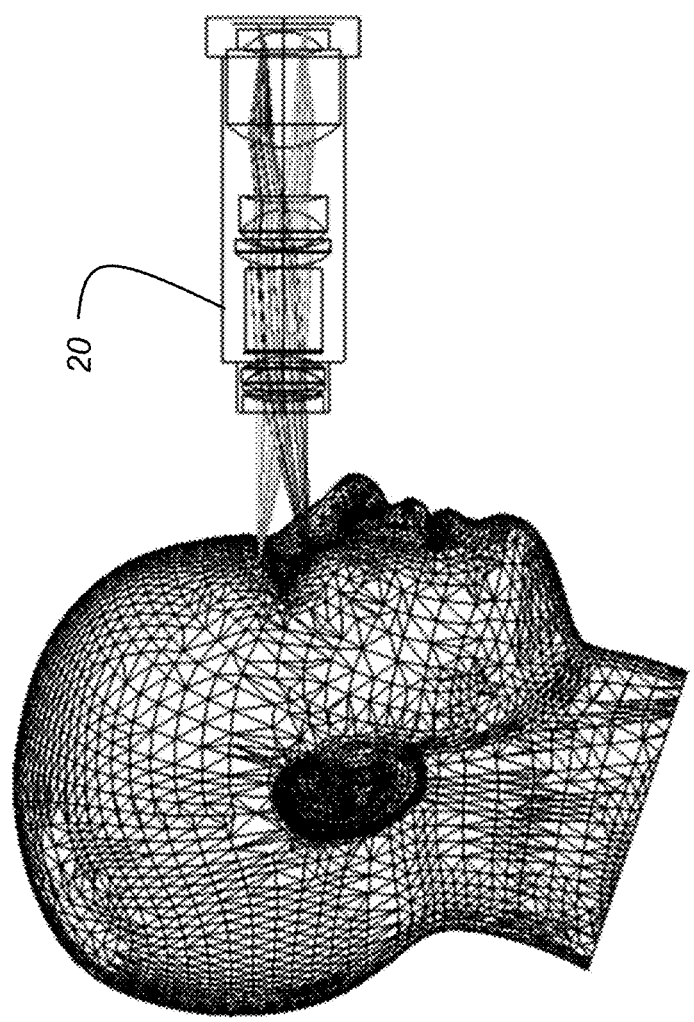
FIG. 6C shows use of the cornea microscope attachment for a seated or standing patient.

Using cornea imaging attachment 20, the viewing practitioner can also open up the full shutter for monoscopic viewing, as shown in FIG. 6C. Monoscopic viewing can be achieved using a single aperture, with variable width for different depths of field, as shown in FIGS. 5C and 5D. To avoid flicker and provide continuous image content, sequential switching can be done at frame rates higher than 50 Hz.

According to one method for obtaining stereopsis, image rendering, whether on a head-worn display or projected or rendered on a display screen, rapidly alternates between left- and right-eye image content, in synchronization with shutter glasses used by the viewer. Alternatively, the dual synchronized signals may be sent to a monitor affixed with lenticular lenses formed on the monitor screen which presents an 3D autostereoscopic view without the need for 3D glasses.

Using the full aperture allows the system to provide high resolution. In addition, the full aperture provides an improved signal to noise ratio (SNR) at the sensor.

The light levels allowed can be limited due to phototoxicity. The brightness at the sensor, in NITs (or $Cd/m^2$), for a perfect system with minimum transmission loss is the same as the brightness at the cornea. However, splitting the aperture in sequential format provides a 3D image with reduced resolution. Alternatively, the aperture image may be split with a prism or other optical splitter so that more than one image sensor may be used to form the 3D image or video.

The power in lumens or Watts collected by the iris is proportional to the iris area. Thus, the best SNR is obtained with its large monoscopic field. The apertures can also be sequentially switched to the different configurations shown in FIGS. 5A, 5B, and 5C, thus providing the surgeon the possibility of a combined image that has high resolution and high SNR.

FIGS. 6A and 6B show the cornea microscope attachment 20 as used in surgery, aimed into the patient eye at different angles to cover different cornea regions. Attachment 20 can be hand-held, with image content provided from the image sensor using either a wired or wireless connection to processor 30 (FIG. 2). Alternately, attachment 20 can be operable for providing image content when mounted directly on the stereomicroscope. An articulated arm (shown in FIG. 15), part of the stereomicroscope apparatus, can be used for mounting, orientation, and aiming of attachment 20.

FIG. 6C shows a side view of use of attachment 20 with a seated or standing patient.

According to an embodiment of the present disclosure, compact cornea imaging attachment 20 can meet the following specifications:

Field at the cornea or iris: 30×20 mm (36 mm diagonal);
Working distance: 61 mm;
Numerical aperture using full aperture: 0.1875;
Pupil size at the shutter: 28 mm diameter;
Sensor size: 30×20 mm;
Nyquist frequency for 6000×4000 pixels: 100 cycles mm;
MTF (average over azimuths) at Nyquist for full aperture: 0.75;
MTF (average over azimuths) at Nyquist for 3D mode: 0.5;

Distortion (grid)<5.4%;
Lateral color: <2 microns;
Total track (vertex to sensor): 150 mm
Prismatic input port size: 32×30 mm.

Figure 6D:
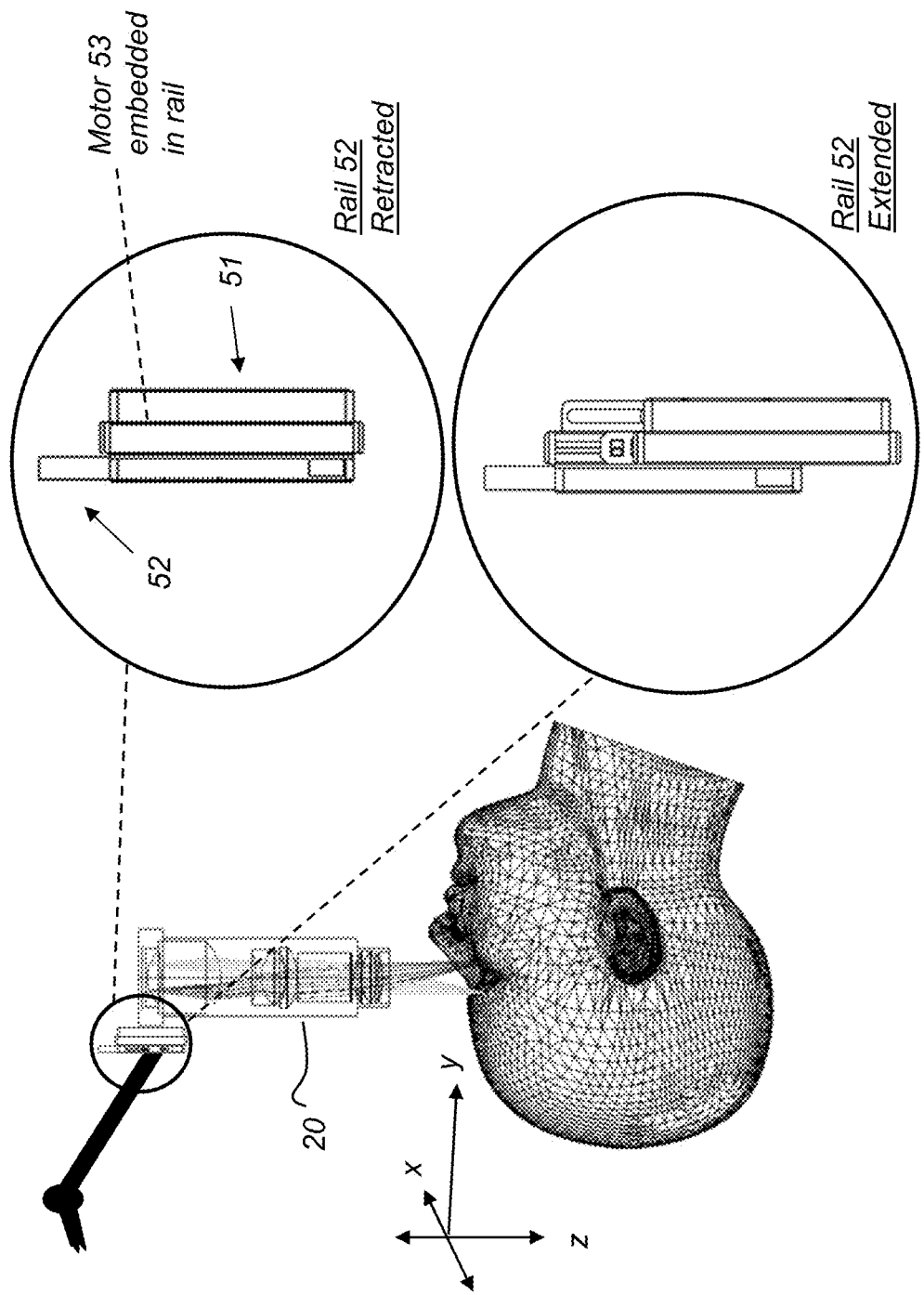
FIG. 6D shows use of the cornea imaging attachment for a prone patient, with the attachment on a robotic arm.
Figure 6E:
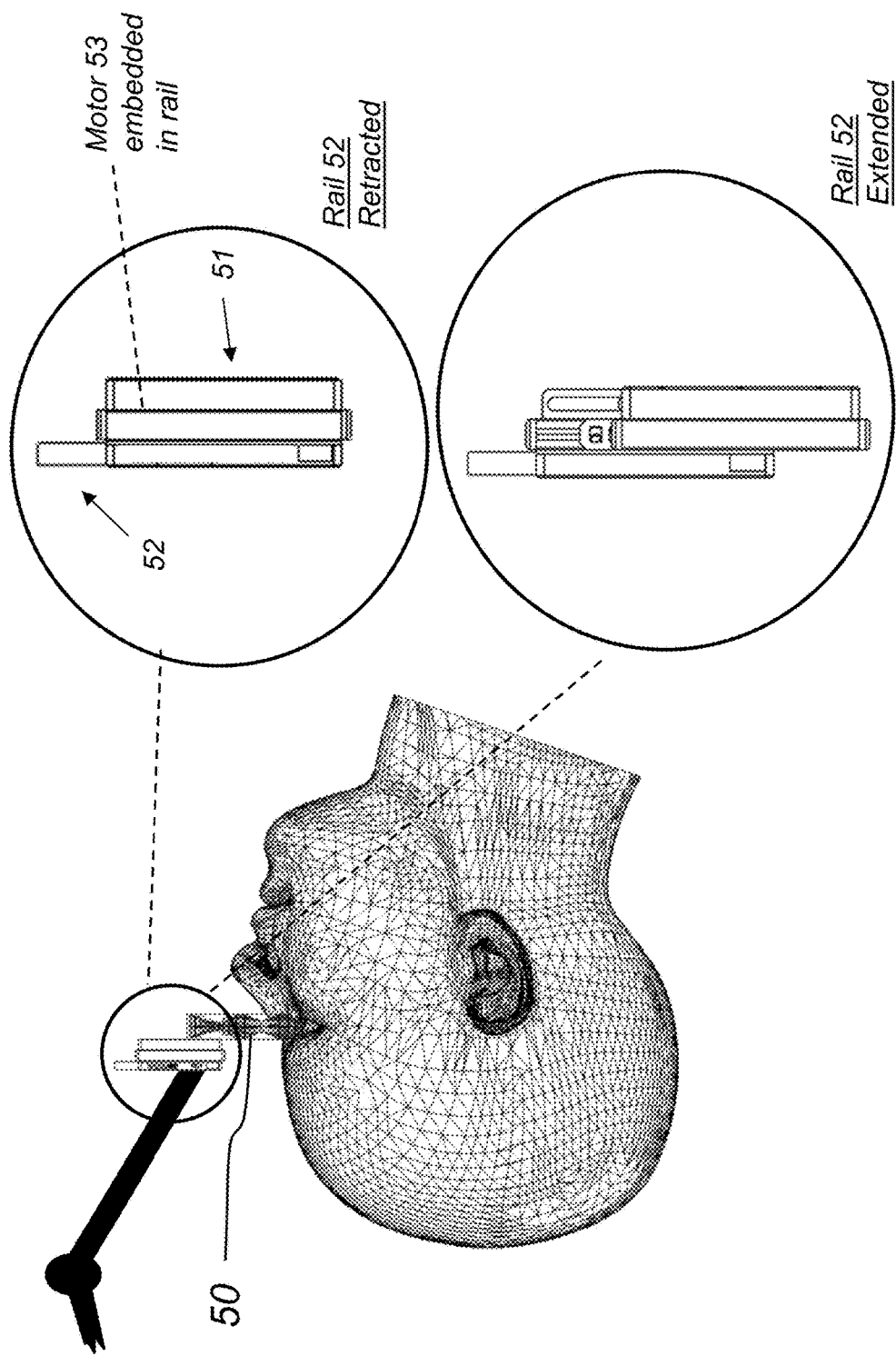
FIG. 6E shows use of a retina imaging attachment for a prone patient, with the attachment on a robotic arm.

The shutter S arrangement allows the surgeon to have either high resolution or increased depth of field. Resolution variation is linear with F/#; depth of field variation is quadratic with F/#. FIG. 6D shows use of the cornea imaging attachment for a prone patient, with cornea attachment 20 held on a robotic arm. FIG. 6E shows alternative use of a retina imaging attachment 50 for a prone patient, with the attachment on a robotic arm.

The use of cobotic technology can allow collaboration of robotic logic and movement with a human operator. Cobotic arms can assist operator manipulation by augmenting their capabilities in terms of effort, assisting the operator to manipulate parts that are heavy, bulky, or too small for precision handling. For example, a surgeon or technician can slightly push the robotic arm in one direction, and the cobotic arm can continue to move to that direction and end up in the intended position, such as returning to a housing location or moving into position at the patient or at the surgeon's eyebox. Similarly, pulling or urging a cobotic arm in a direction can cause continued movement until the arm reaches a predetermined position. Optionally, actuators in the microscope can automatically move the cobotic arms and microscope and camera tools toward the surgeon's eyes, in response to either hand gesturing or voice command, for example.

As described herein, the microscope of the present disclosure can use both optical-mechanical and digital zoom. The optical zoom is accomplished by a combination of optical lenses with adjustable focus, mechanical parts which adjust multiple lenses to either increase or decrease the distance between lenses to provide more or less magnification. Optical zoom components may also include electronic controls to activate, reverse, or hold lens positions. In another embodiment, an apparatus for additional focus is described that can be especially useful when at high optical-mechanical and digital magnification, wherein finer focus can be achieved by use of an adjustable "z" axis platform, driven by either a manual or electronically adjusted micrometer head. (Exemplary axis assignments are shown for reference in FIG. 6D). As is well known in the art, a micrometer head is a common device used for fine measurements, or positioning. The micrometer head, in this instance, is affixed to a vertical, z-axis rail, whereby it can be translated along the optical axis, towards or away from the optical object, to adjust focus in a precise manner. In one embodiment, a manual micrometer head 51 of FIGS. 6D and 6E can be affixed to a vertical rail 52 in a telescoping fashion, retracted or extended as needed to provide fine high-resolution focus. Micrometer head 51 can be controlled either manually or by electronic activation in combination with a model controller of the microscope via a small motor 53, working attendant to the movement on rail 52. Electronic actuation can be in response to operator instructions or can be automated according to programmed or learned logic executed by the model controller of the microscope.

Figure 7A:
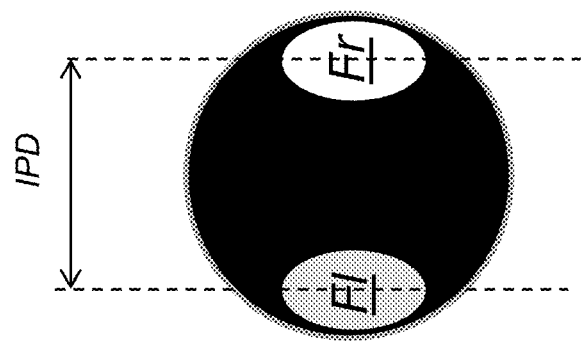
FIGS. 7A and 7B show an aperture mode with adjustable stereopsis.
Figure 7B:
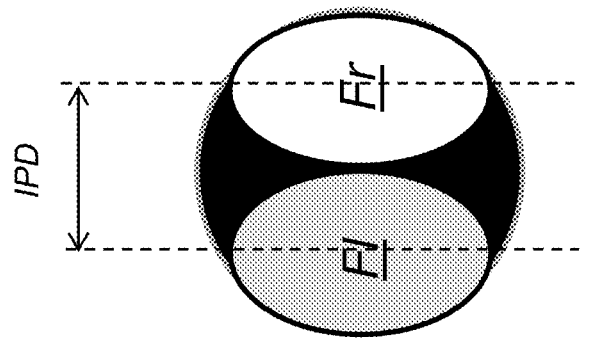

FIGS. 7A and 7B show an aperture mode allowing adjustable stereopsis, employing shutter S to adapt stereopsis to the viewer's sensed inter-pupil distance (IPD) by modifying the shape and relative location of the left and right field portions Fl and Fr. This solution can improve 3D perception and depth of field at the cost of some loss of resolution and decrease in signal-to-noise ratio (SNR).

Figure 8B:
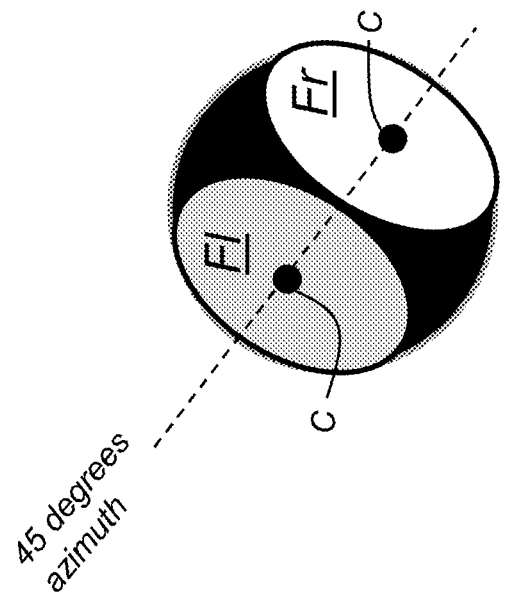
FIGS. 8A and 8B show an aperture mode with adjustable IPD azimuth.
Figure 8A:
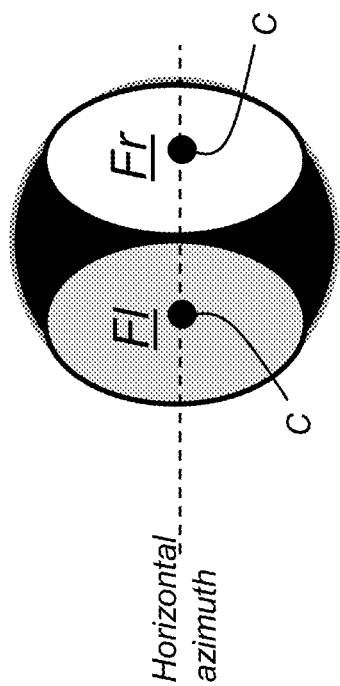

Another feature provided with the apparatus of the present disclosure relates to the possibility of changing the inter-pupil azimuth, as shown in FIGS. 8A and 8B. FIG. 8A shows a horizontal azimuth, at a 0-degree default. FIG. 8B shows an alternate arrangement of Fl and Fr field portions from a sub-apertures arrangement providing a 45 degree azimuth, defined from a center C of Fl to center C of Fr, for example. Other oblique azimuth angles can alternately be used.

Other azimuth angular arrangements are possible at suitable angular increments using control of the spatial light modulator that defines the apertures. This capability for re-positioning and adjusting aperture position and size enables improved 3D perception of various structures, including inclined narrow structures such as the edge of tear or a thin film of tissue that could be otherwise difficult to perceive without angular change and, optionally, change to aperture shape and size. Likewise, by using the azimuth angular offset or rotation, other defects such as lens detachment, or positioning or adjustment of an Intraocular Lens (IOL) may be more easily determined. The viewing practitioner can use audible, gestural, or command console instruction entry to adjust the azimuth angle.

Figure 9B:
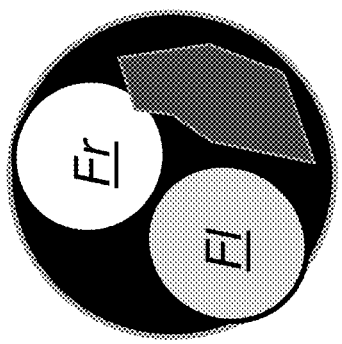
FIGS. 9A and 9B show an aperture mode adjusted to avoid cornea defects.
Figure 9A:
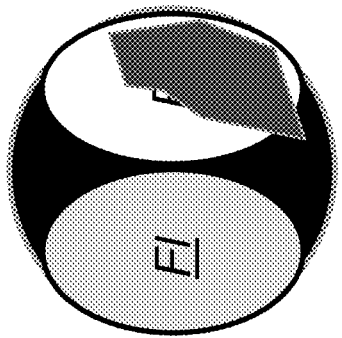

Another feature of the current disclosure is capability to adjust the sub-apertures at the iris to avoid cornea defects or cataracts as shown by changing size and position of apertures for left and right-eye fields Fl and Fr between FIGS. 9A and 9B. According to an embodiment of the present disclosure, processor 30 logic is programmed or trained to detect cataracts or other defects that obscure practitioner view and to automatically adjust the azimuth angle accordingly. The amount of angular azimuth offset from horizontal can display on the display monitor or headset display to inform the viewer of the adjustment setting.

An alternate method for extending the depth of field uses Extended Depth of Field (EDOF) filters. These filters, as described, for example, by Cathey et al. in US Patent Application Publication No. 2008/0174869 A1 entitled "Extended Dept of Field Optical Systems", can be placed symmetrically, one for each left- and right-eye portion Fl and Fr. Exemplary filters used for extending depth of field can be, for example, phase plates having significant aberration, such as elliptical coma, wherein the image is degraded in a known manner, to be retrieved by processing over a larger depth of field.

The device of the present disclosure can also be used to provide volumetric imaging which is currently termed temporal light field imaging. This feature allows for the sensor to be moved incrementally along its z axis, parallel to the optical axis OA, preferably in the monoscopic imaging mode, by an actuator 34 (FIG. 2) thus exploring the cornea and iris at different depth locations. The volumetric information thus retrieved can be rendered into stereoscopic information and presented to the surgeon as 3D stereoscopic cornea images. Instead of moving the sensor over a number of z-axis positions, a variable phase element can be disposed at the imaged iris in order to provide the desired variable focusing.

Figure 10:
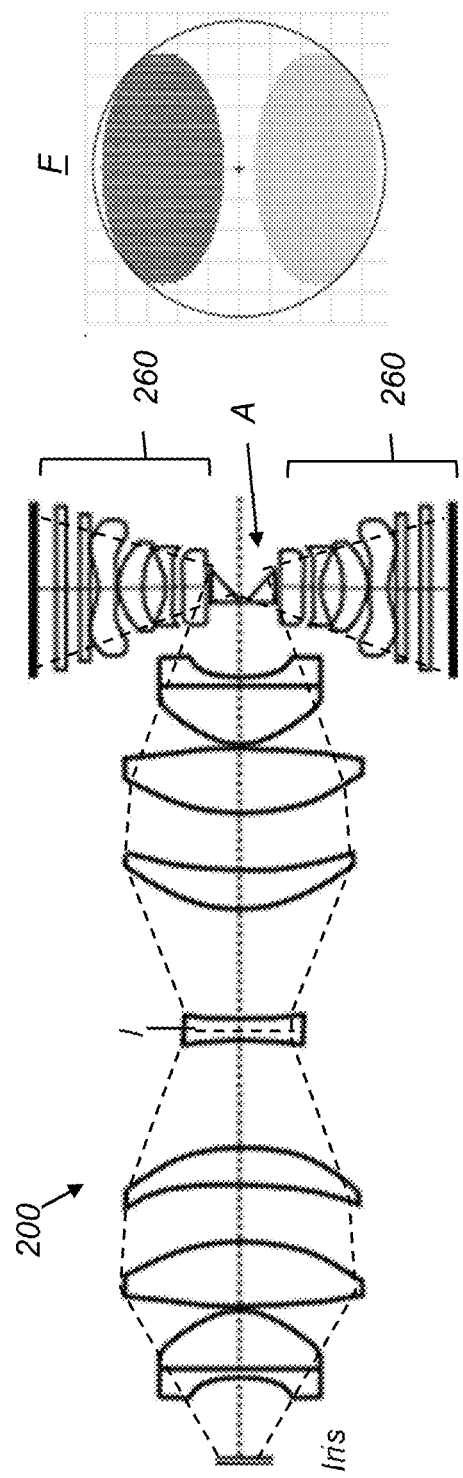
FIG. 10 shows use of two cameras in an alternate embodiment.

In another embodiment of the present disclosure, as shown in FIG. 10, the 3D information is retrieved by using an iris relay that forms an intermediate image I, followed by a pupil splitter and then two cameras 260 or other sensors, one for the left-eye view and another for the right-eye view. However, in this embodiment, the two 3D channels cannot be modified by using the shutter model described previously, nor is the full aperture of the objective available for imaging.

The system is similar to the conventional design, but can be significantly more compact, has no eyepiece, and is readily maneuverable.

Illumination Options

Figure 11:
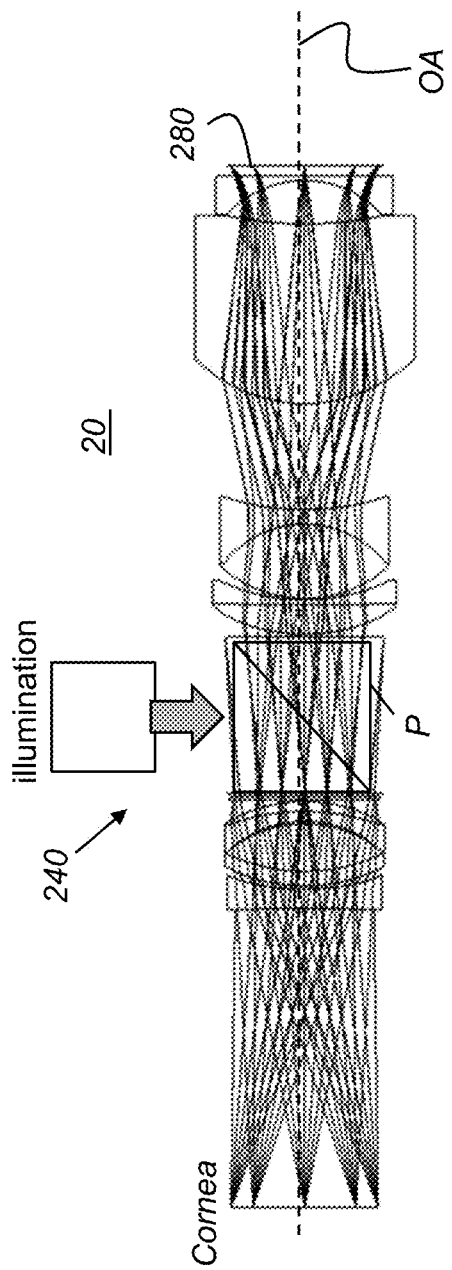
FIG. 11 is a side view schematic showing the use of auxiliary illumination with the corneal imaging attachment.

A shutter and input port subsystem 240, such as using a combiner prism P, can be used to support a number of auxiliary options, providing access to the optical axis of the microscope apparatus. FIG. 11 show an illumination source directing light through the input port of combiner prism P. Alternatively, a separate lamp similar to the halogen lamp on a slit lamp can be used to illuminate the cornea or iris. In another alternate embodiment, ring illumination can be provided with a ring mounted on or near the front lens element. The ring illumination may be an LCD and may be connected to the Model Controller for the viewing system.

Figure 12A:
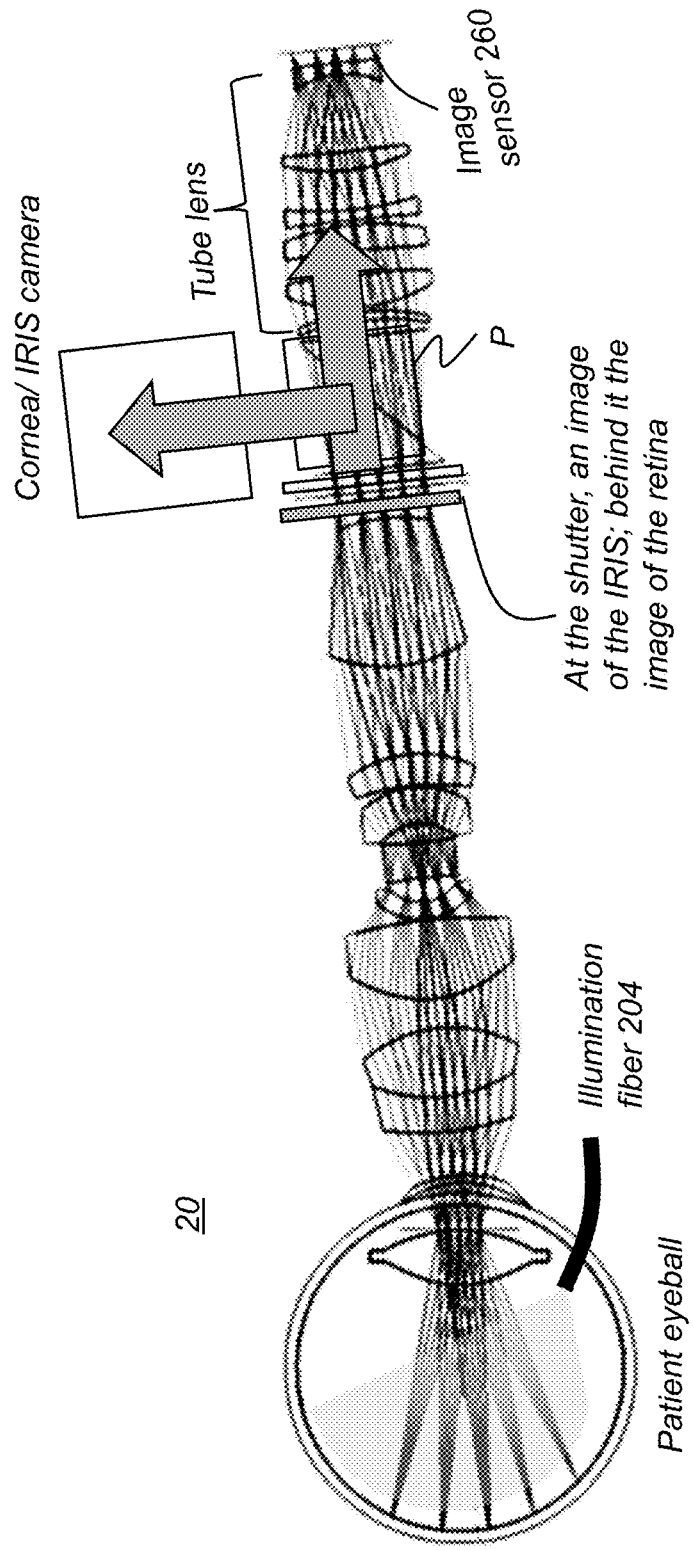
FIG. 12A is a schematic view showing the use of an auxiliary cornea camera with a retinal imaging attachment.

The system can be used in combination with a retinal imaging system, as is shown, for example, in the side-view schematic of FIG. 12A. An illumination fiber 204 can provide light to the retina. Combiner prism P can combine light paths for retina and cornea imaging along a single optical axis.

Figure 12B:
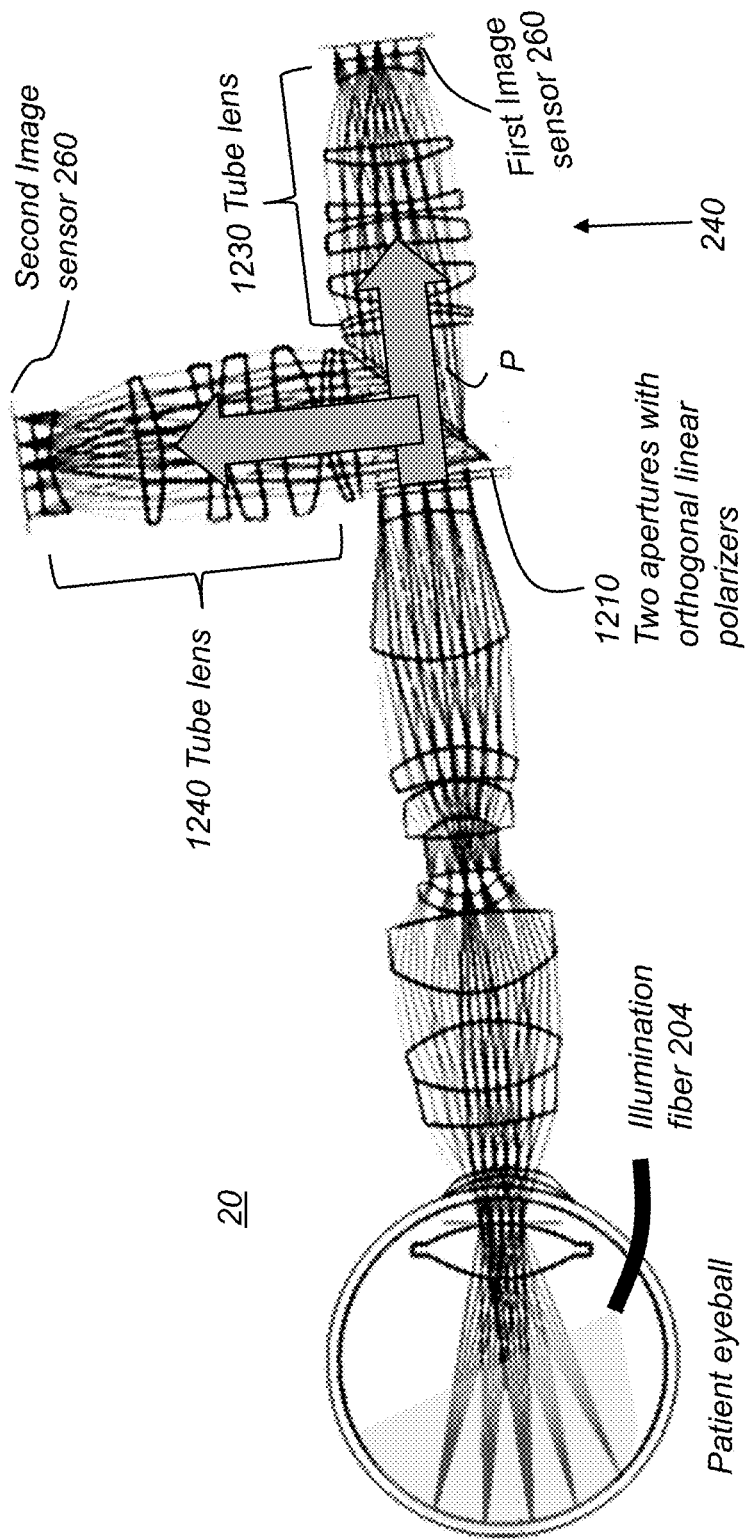
FIG. 12B is a schematic view showing the use of an auxiliary cornea camera with a retinal imaging attachment and two tube lenses.
Figure 12C:
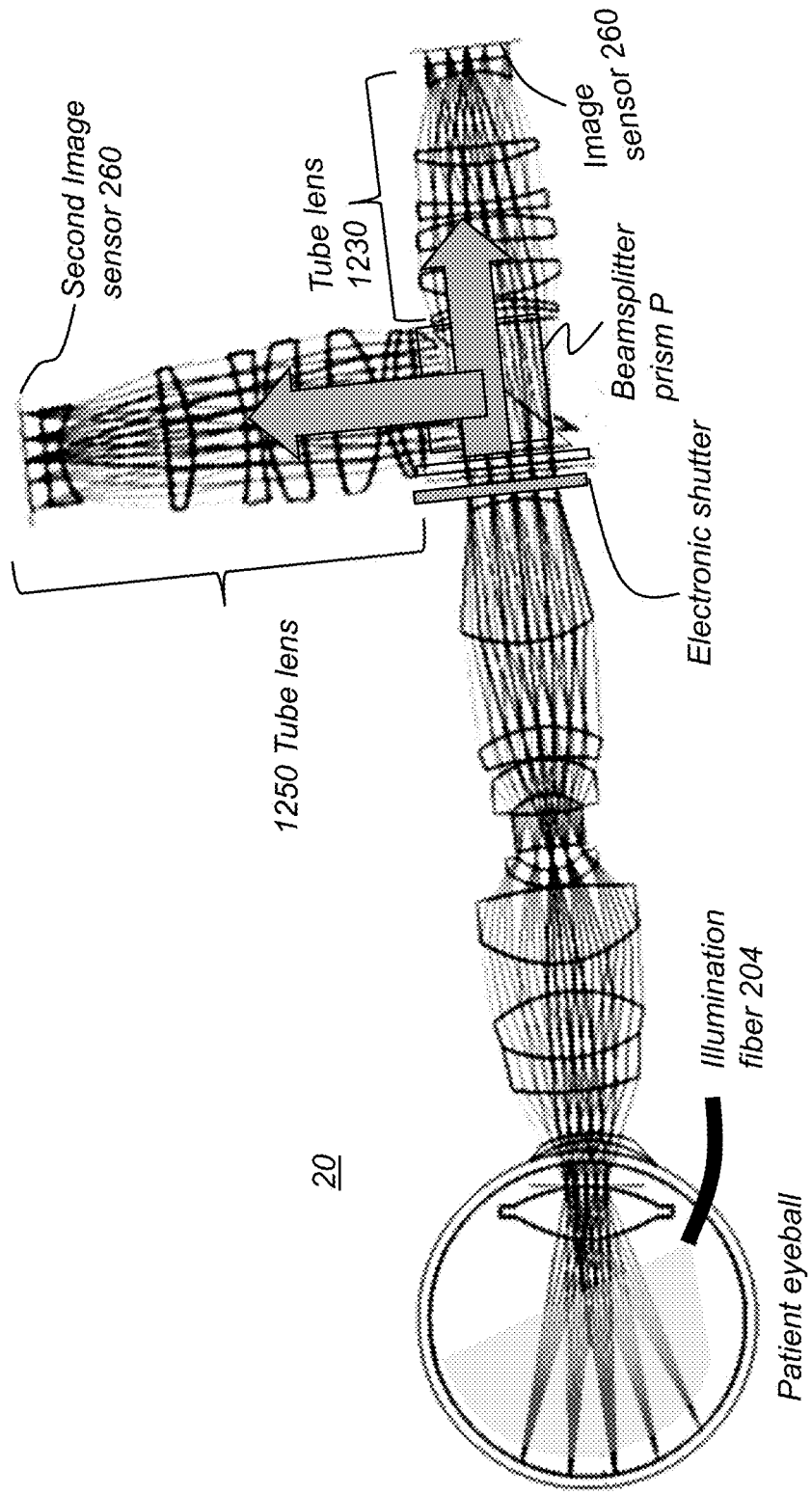
FIG. 12C is a schematic view showing the use of an auxiliary cornea camera with a retinal imaging attachment and two tube lenses according to an alternate embodiment.

Alternately, or in concert with the above, as shown by FIG. 12B, the system can form 3D images using an additional external sensor. In this instance, the electronic shutter of FIG. 12A can be replaced by two fixed apertures 1210, each aperture 1210 having a corresponding polarizer, wherein the polarization states of the polarizers are orthogonal to each other, and wherein the beam splitter cube of FIG. 12A, is replaced by a polarizing beam splitter cube P thereby directing a first optical channel to a tube lens 1230 and the first camera sensor 260; and directing the second optical channel to a second tube lens 1240 and second camera sensor 260. In another embodiment, as shown in FIG. 12C, is a configuration wherein a two-sensor optical connection as in FIG. 12B is used, wherein the electronic shutter remains, however the tube lens 1250 to the first sensor of FIG. 12B is a different length to be configured to image the retina, while the second tube lens 1230 is configured to image the cornea simultaneously in 3D.

Figure 13A:
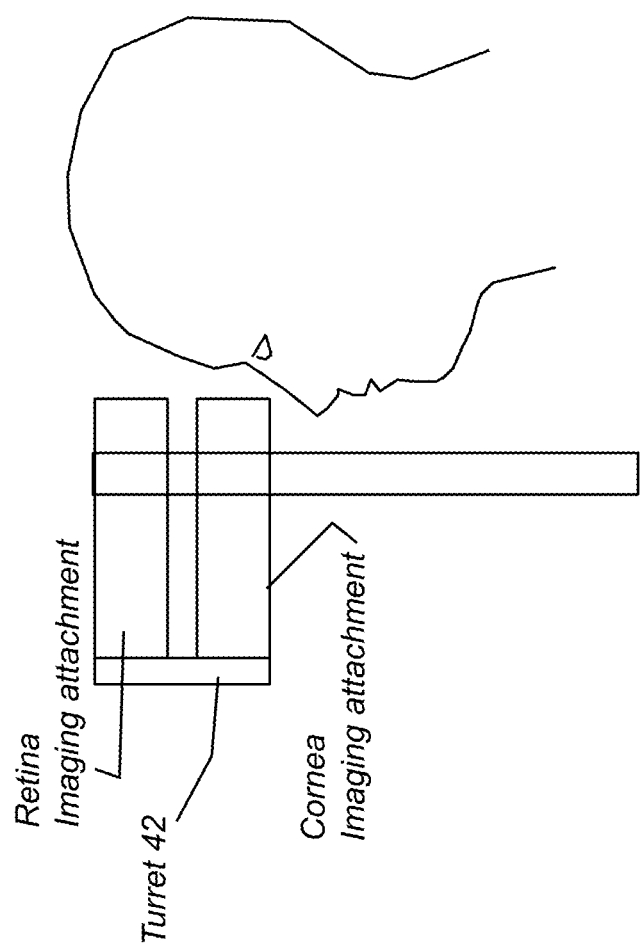
FIG. 13A is a schematic that shows a system for office examination having a retina imaging attachment and a cornea imaging attachment on a turret.

The system may use a combination of elements or two systems mounted adjacently on a microscope turret, as shown in FIG. 13A. The cornea imaging attachment described herein can be used as a standalone imaging device for forming an image on sensor 260; a standalone configuration is typically useful for office examination by the practitioner. When mounted as part of a larger imaging system, the cornea imaging attachment can be mounted in the turret 42 of FIG. 13A or other type of switching device and used to automate office examination imaging as well as for imaging during surgical procedures. Robotic actuators, not shown, can be used to position and increment the imaging attachment at different angles for obtaining more complete imaging content. Cooling devices, such as thermoelectric cooling (TEC) components can be used for heat management of the sensor and other sensitive components.

Figure 13B:
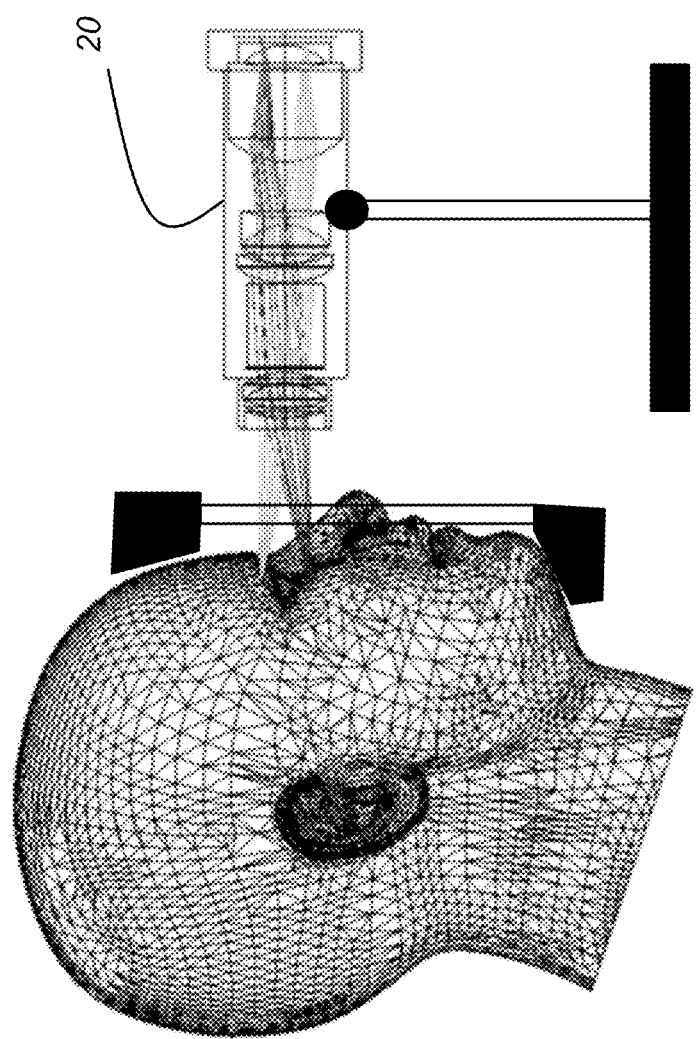
FIG. 13B shows use of the cornea imaging attachment for a vertical patient.

FIG. 13B shows use of the cornea imaging attachment 20 for a vertical patient.

Figure 13C:
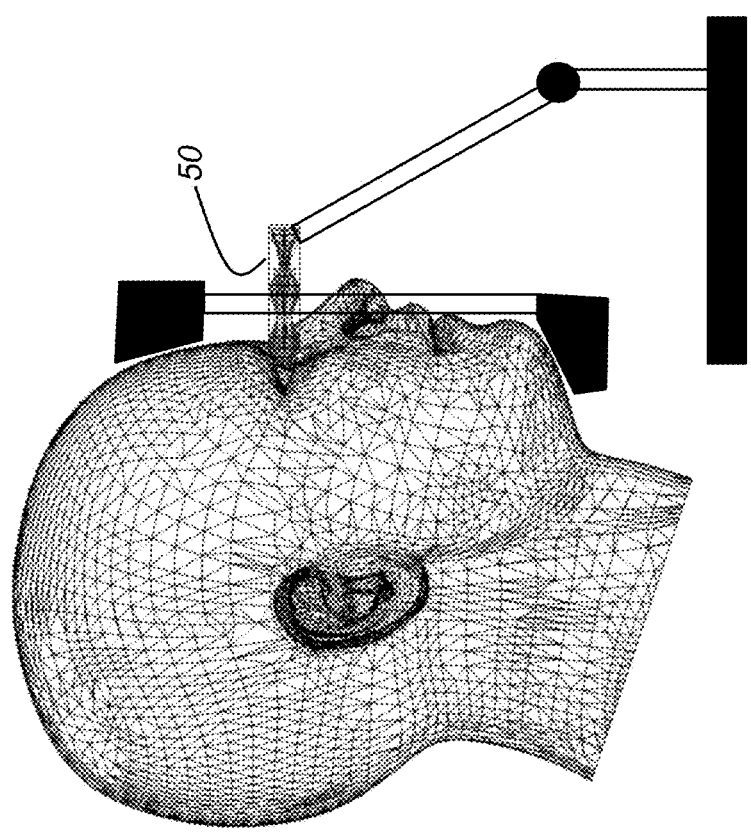
FIG. 13C shows use of a retinal imaging attachment for a vertical patient.

FIG. 13C shows use of a retina imaging attachment 50 for a vertical patient.

Tables 1 and 2 give design data for a cornea imaging attachment of FIG. 11 according to an embodiment. Full field of view at the cornea/iris is 30×20 mm. Numerical aperture at the cornea is 0.1875. The design is corrected over the visible range.

Visualization Options

Digital imaging, as provided by the Applicant's stereomicroscope apparatus, offers a number of visualization options for surgeon selection, including conventional microscope viewing, use of high-resolution video, and wearable augmented reality (AR) devices.

FIG. 14 shows an AR headset 60 for viewing images of the cornea and related features. Headset 60 can include cameras and other sensors 62 for obtaining viewer instructions from the surgeon or other practitioner. Extended reality (XR) viewing can also be provided, including Mixed Reality (MR), and Virtual Reality (VR). Headset 60 can include micro-displays, head tracking, eye-tracking, and depth-sensor cameras to display images to the wearer, effectively providing the illusion of augmented reality.

FIG. 15 shows an autostereoscopic 3D monitor 70 of the present disclosure that provides 4K video and 3D Holographic image output for the patient cornea using a stereomicroscope apparatus 100. Display presentation can be with or without polarized 3D glasses or shutter glasses. Image presentation is at high resolution and suitably positioned for viewing by the surgeon, without requiring turning of the head for a surgeon and others on an operating room team. Cornea attachment 20 can be provided on an articulated arm 110, for example.

Figure 16:
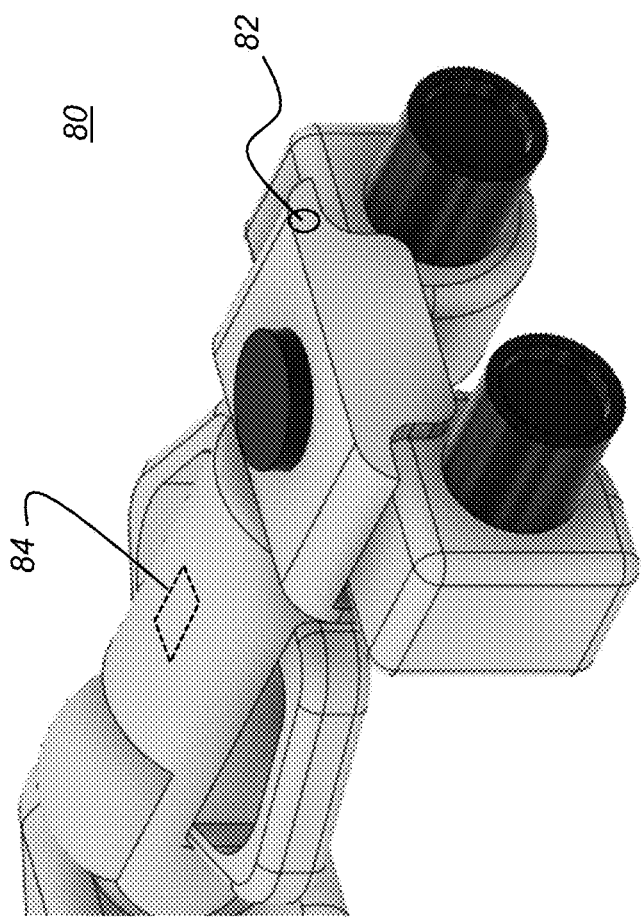
FIG. 16 is a perspective view that shows microscope viewing optics that can be used for visualization with the stereomicroscope apparatus.

FIG. 16 is a perspective view that shows microscope viewing optics 80 that can be used for visualization with the stereomicroscope apparatus. Each eye piece can have high resolution, such as 4K resolution with full color 3D imaging, from the digital surgery feed. Sensors 82 in viewing optics 80 are used to sense surgeon position, allowing actuators 84, such as motors and associated components, to extend the viewing optics 80 to reach out for the surgeon's head/eyes and stop just short of the surgeon's position. Sensors 82 can include cameras or infrared sensors, for example. This enables the surgeon to change positions during surgery, while viewing optics 80 follow the surgeon's posture without the need for manual adjustment or touch.

Voice plus Eye-Tracking redundancy for the various display options can help to provide the surgeon with control of tools using gaze tracking or audible commands, for hands-free operation.

Figure 17:
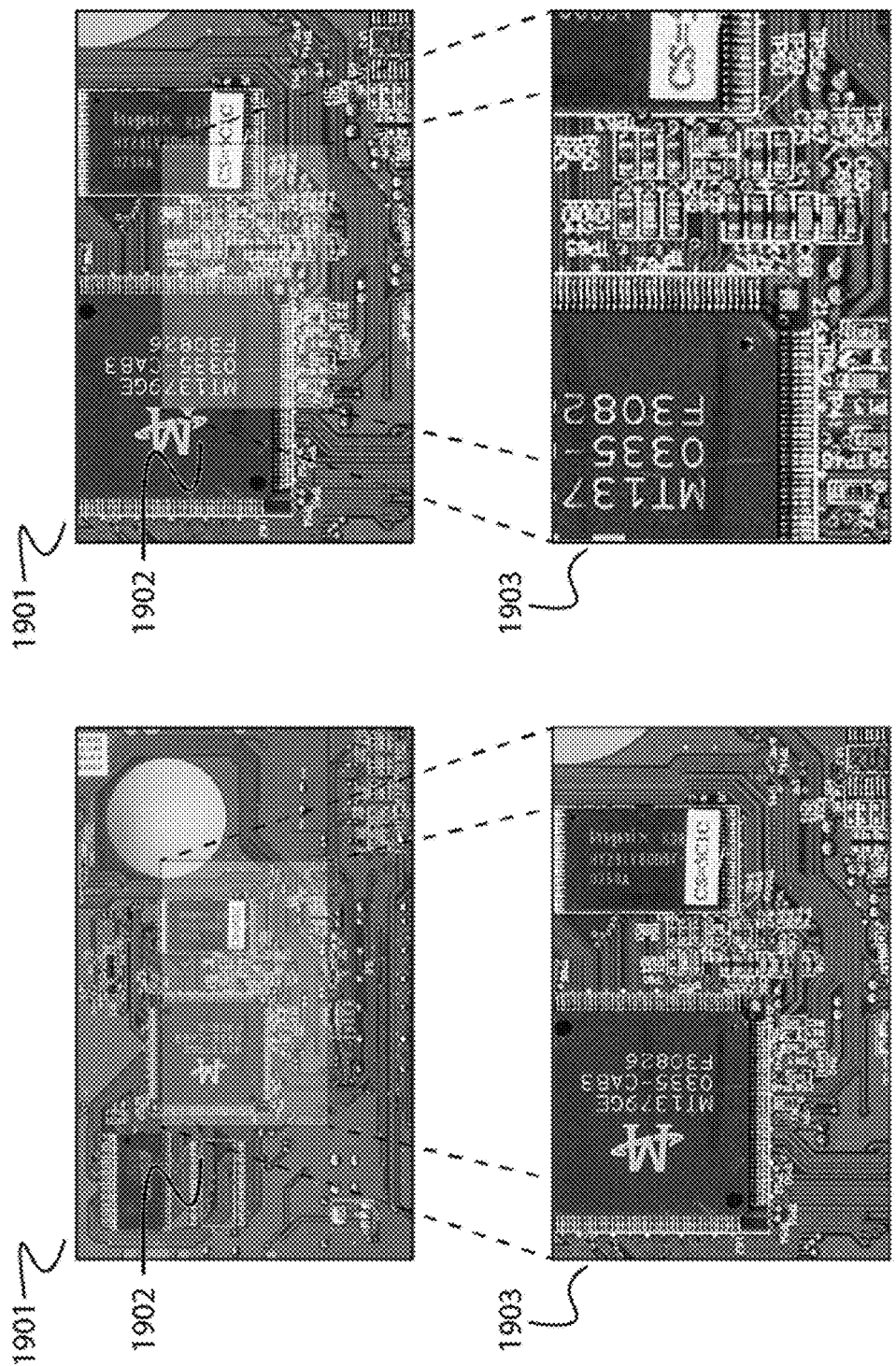
FIG. 17 shows an example of digital zoom.

Referring to FIG. 17 by way of example, "digital zoom" is a method of decreasing the precise angle of view of a digital photograph or video image by taking a subset of the pixels. Digital zoom is accomplished by cropping a subset of the pixels from the original image 1901 while keeping the same aspect ratio on the subset image 1902 as the original and then scaling the subset image 1902 back up to the original dimensions of the original image 1901. These processes can be repeated until the resolution is so low that the image quality does not justify further digital zoom magnification, which would be when the cropped and enlarged image reaches the same pixel size as the image sensor(s). This typically occurs when the cropped and enlarged image has the same resolution as the display(s) used, as in image 1903. For example, digital zoom can terminate when the final cropped and enlarged image is 4K (3,840×2,160 at 16:9 aspect ratio) and is the same as the display(s).

Figure 18:
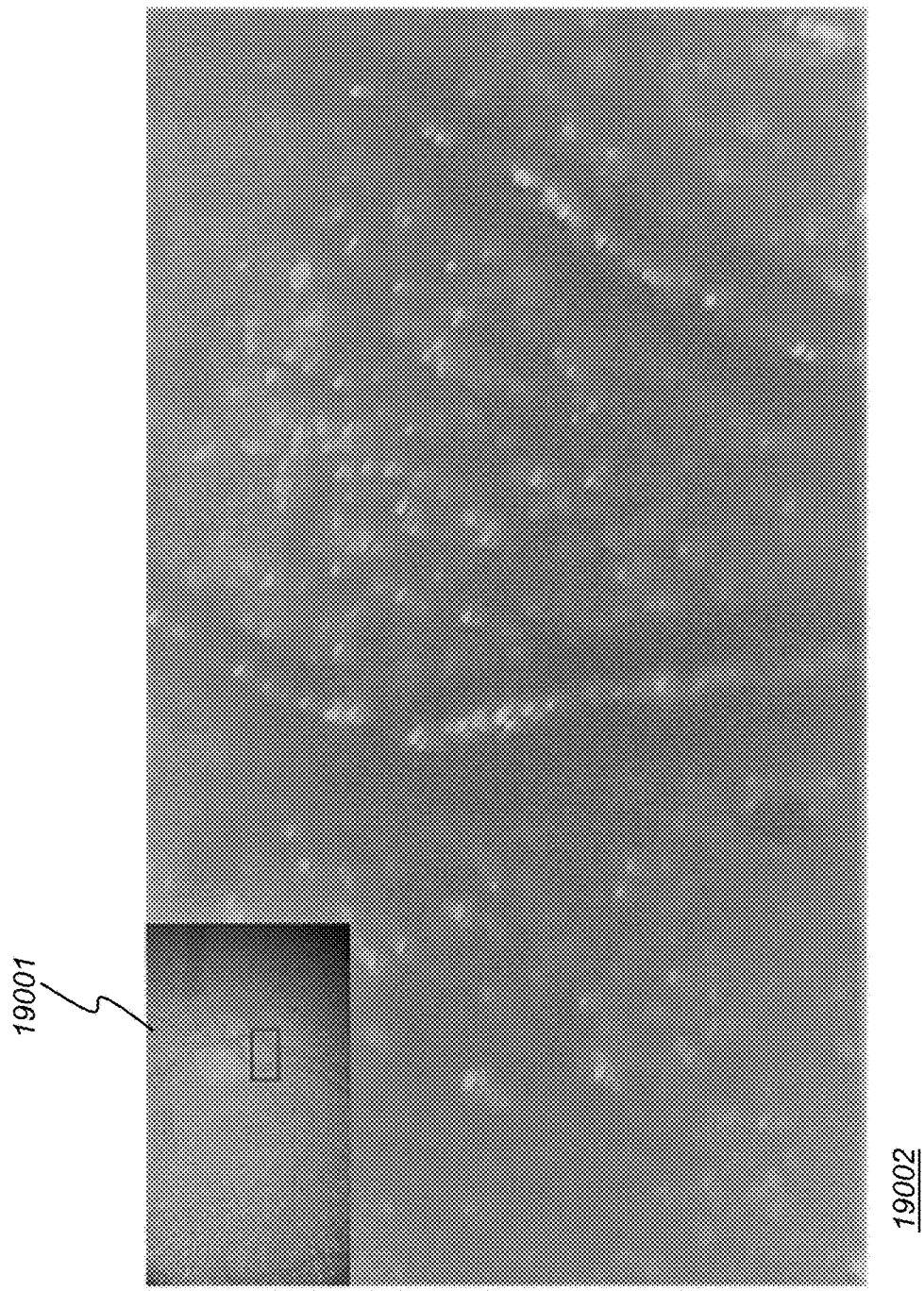
FIG. 18 shows picture-in-picture capability.

FIG. 18 depicts a picture-in-picture (PnP) feature of the device. When the surgeon begins to zoom in or magnify an image or area, the controller may be prompted to begin forming an image-within-image, or a picture-in-picture, which may appear as an image 19001 in the corner of the larger magnified image 19002, while the larger picture is the actual magnified image 19002. The PnP may allow the viewer to keep their orientation and understand where they are located within the whole image so as not to lose orientation to the larger structure.

This utility is designed to simplify identifying where the viewer is (i.e., in an area of the retina) in relation to the non-zoomed image. This feature may permit the surgeon to examine the same region of the image with different zoom levels or different angles, with respect to the whole image before it was magnified.

Through software and the controller, each image may be a dynamically linked map that follows along the same coordinates. Changing the coordinates of the center on one of them may lead to an automatic displacement of the center in the same point of the second, and a coordinate display unit informs of the current coordinates. Thus, when a user begins to magnify or zoom in on an image or video, a secondary rendering of the image may appear on the lens of the viewport, and the larger, magnified image may become the primary image.

The primary image may be magnified as specified by the user, while the secondary image may capture the original coordinates of the primary image before it was magnified. Through software control and menu selection, the secondary image can be pinned to either the top left corner, top right corner, bottom left corner, or bottom right corner depending on the surgeon's preference, or as a preset, and can be shifted to a new location using touch commands on the internal display, which may be a touch screen, or by other control.

The secondary image may be a digitally altered subsampling of the primary image. Thus, the secondary image may fill the viewport showing an inspector their region of interest, while the primary image may be placed in a corner of the viewport to serve as a map. The position of the secondary image may then be indicated on the primary image via an overlay, whether varying capacity monochrome or color. Digital altering of the primary image can include digital zooming, color contrast enhancement, color picking, or other video processing system that is useful for the surgeon.

The system computing and controller can also present imaging or video in "Picture-in-Picture" technology in the microscope instrument which may permit a surgeon or user of any of the 3D displays mentioned herein to watch two images or videos (primary and secondary) simultaneously. Thus, the surgeon could simultaneously see imaging from two separately images. The primary image may fill the entire screen or projection across a display, while the secondary image may be a smaller (approx. ¼th of the primary image size), floating window pinned to a corner of the screen (always on top of all other windows), which may allow users to keep an eye on what is happening in both images at one time. This may be especially helpful if the surgery is near or adjacent to an especially vulnerable organ. Thus, the surgeon could see the (larger) image of the cutting, ablation, or resecting, watching from another angle to how close the instrument is to a vital or vulnerable organ.

In addition, to reduce the signal noise so that the quality of the image remains as sharp as the original, pixel-binning may be used. Pixel-binning is a process where a clocking scheme is used to combine the charge (light) collected by several adjacent pixels to reduce the "noise". Noise in this instance is a random variation of brightness or color information in images and is usually an aspect of electronic noise which is generated by the digital camera sensors. To correct for this "noise" upon digital magnification, pixel-binning can be used whereby the viewer can obtain the best detail in good lighting conditions, while also being able to produce high-quality low-light shots. The high-quality low-light video or image is formed by sampling multiple pixel's light. The sensor or sensors chosen for the microscope contain the largest pixel size possible or available. Thus, the larger a sensor's pixels (or photosites), the greater the light-gathering ability, which is axiomatic. However, it can take a significant number of pixels to render images in high resolution. The size of a photosite is called the pixels' "pixel pitch", which is measured in microns. Thus, a larger micron pixel has a higher pixel pitch. Because not all photosites collect the same amount of light (red, green, and blue) pixel-binning is used to sum the signals of adjacent pixels to enhance the resolution and increase the signal-to-noise ratio. The resolution is enhanced because the higher the signal to noise ratio, the clear the definition is and the more the boundaries between different color and brightness of the pixels is evident. Thus, the combination of digital zoom and pixel-binning permits the zoom feature to go far beyond what optical zoom alone can do. This is one of the major benefits of digital zoom.

Figure 19:
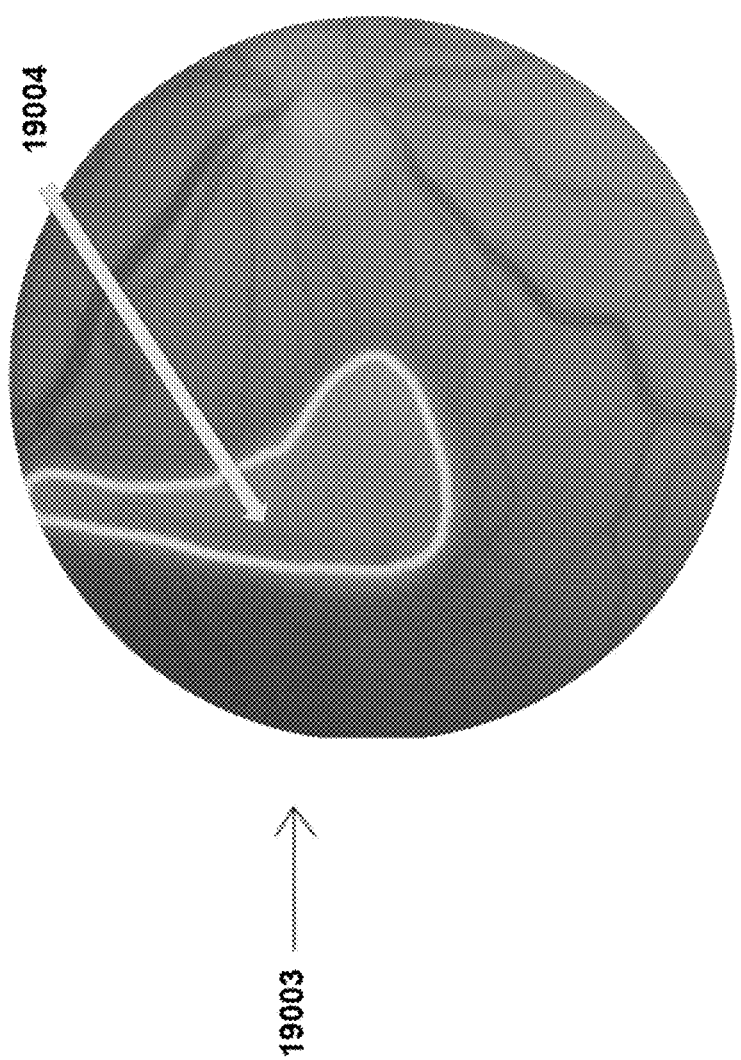
FIG. 19 shows picture-on-picture capability.

As shown in FIG. 19, another capability of the system is to form picture-on-picture (PoP) images wherein an existing video feed 19003 has a digital overlay 19004 of pre-designated or real-time generated by the computer controller origin is added to an existing 2D or 3D video or still shot surgery feed. The advantage of this setup is that, the system can take the signal and render image content overlayed in multiple display medias, in a connected telemedicine method, including displaying the video remotely in the instance of expert-assisted surgery, where addition video, imagery or test is overlayed on the existing video feed. Thus, a remote surgeon, team, or another viewer could visualize the internals captured by the cameras and assist the surgeon physically onsite with information, advice, instruction, or caution by touch or 6 DoF (degrees-of-freedom) sensing to show a marker overlayed on the surgery video feed. Picture-over-picture is a method in which any number of image classification and bounding techniques may be used by the computer system to understand the importance of an object in the field. This can be achieved by using high color depth sensors to better determine objects that are minimally viewable.

On PoP, when a bounding area is defined on the video containing that object, the computer system may then use edge detection, and other computer vision techniques to highlight the specific region of interest in the video. This highlighted portion is the overlaid-on top of the video as captured by the camera sensors at the point of the computer system so that the picture-over-picture image is displayed to the viewer on the monitor, etc.

Whereas, the devices and methods have been described in relation to the drawings and claims, it should be understood that other and further modifications, apart from those shown or suggested herein, may be made within the spirit and scope of this disclosure.

The apparatus of the present disclosure has been described in detail with particular reference to a presently preferred embodiment, but it will be understood that variations and modifications can be effected within the spirit and scope of the disclosure. The presently disclosed embodiments are therefore considered in all respects to be illustrative and not restrictive. The scope of the invention is indicated by any appended claims, and all changes that come within the meaning and range of equivalents thereof are intended to be embraced therein.

The invention claimed is:

1. An apparatus for obtaining an image of a cornea comprising:
 a digital microscope configured to obtain 2D and 3D anterior imaging content of an eye of a patient, the digital microscope including:

a cylindrical housing;
an optics system positioned within the cylindrical housing and configured to form an optical pupil along an optical axis, the optics system including:
an image sensor configured to receive light along the optical axis;
an actuator coupled to the image sensor and configured to move the image sensor along the optical axis;
a shutter disposed at an objective of the digital microscope and configured to form a pattern of one or two apertures for light along the optical axis;
a tube lens disposed to direct light from the shutter to the image sensor;
a combiner prism positioned along the optical axis and including an input port disposed between the shutter and the tube lens, the combiner prism configured to combine light from one or more imaging subsystems or sources onto the optical axis; and
a slit lamp light source aiming light through the input port of the combiner prism at a cornea;
an articulated arm coupled to the cylindrical housing for supporting the digital microscope for aiming the digital microscope at different pointing directions to the eye of the patient; and
a control logic processor operably coupled to the shutter and the actuator, and programmed to perform an algorithm including the steps of:
operating the shutter to alternate between left-eye content and right-eye content;
operating the actuator to move the image sensor incrementally along the optical axis; and
transmitting images formed by the image sensor to an imager.

2. The apparatus of claim 1 wherein the shutter is configured to define a first shutter aperture for a left-eye image and a second shutter aperture for a right-eye image.

3. The apparatus of claim 2 wherein the first and second shutter apertures are disposed horizontally with respect to each other.

4. The apparatus of claim 3 wherein spacing between the first and second shutter apertures is variable according to instructions from a viewer.

5. The apparatus of claim 4 wherein the shutter is further configured to form a single aperture for monoscopic viewing.

6. The apparatus of claim 3 wherein the control logic processor is configured to vary an azimuth angle defined from center to center of the first and second shutter apertures.

7. The apparatus of claim 2 wherein the control logic processor is further configured to vary an eccentricity of elliptical first and second shutter apertures.

8. The apparatus of claim 1 wherein the shutter is a liquid crystal device.

9. The apparatus of claim 1 wherein the shutter is a micro-electromechanical systems device.

10. The apparatus of claim 1 wherein the digital microscope is coupled to a stereomicroscope via a vertical rail.

11. The apparatus of claim 1 further comprising an audio sensor in signal communication with the control logic processor.

12. The apparatus of claim 1 further comprising a camera coupled to the control logic processor and configured to acquire a gesture that indicates a viewer instruction to control an aperture pattern of the shutter.

13. A method of obtaining anterior images from different directions comprising:
providing a digital microscope including:
providing a cylindrical housing;
providing an optics system positioned within the cylindrical housing and configured to form an optical pupil along an optical axis, providing the optics system including:
providing an image sensor configured to receive light along an optical axis;
providing an actuator coupled to the image sensor and configured to move the image sensor along the optical axis;
disposing a shutter adjacent to a microscope objective, wherein the shutter is configured to form a pattern of one or more apertures for light at an optical pupil;
providing optics configured to convey light through the shutter and along the optical axis to the image sensor;
disposing a tube lens to direct light from the shutter to the image sensor; and
disposing a combiner prism along the optical axis including an input port between the shutter and the tube lens, wherein the combiner prism is configured to combine light from one or more imaging subsystems or sources onto the optical axis;
providing a slit lamp light source aiming light through the input port of the combiner prism at a cornea;
providing an articulated arm coupled to the cylindrical housing for supporting the digital microscope for aiming the digital microscope at different pointing directions to the eye of the patient;
operating the shutter to alternate between left-eye content and right-eye content;
operating the actuator to move the image sensor incrementally along the optical axis;
obtaining and recording anterior imaging data from the image sensor; and
transmitting the imaging data to an imager.

14. The method of claim 13 further comprising forming a first aperture for left-eye viewing and a second aperture for right-eye viewing.

15. The method of claim 14 further comprising adjusting spacing between the first and second aperture.

16. The method of claim 14 further comprising automatically adjusting an azimuth angle between the first and second apertures to be offset from horizontal.

17. The method of claim 13 further comprising:
receiving a gestural command via a camera; and
responding to the gestural command by forming a first aperture for left-eye viewing and a second aperture for right-eye viewing.

* * * * *